US009808509B2

(12) United States Patent
Frey, II et al.

(10) Patent No.: US 9,808,509 B2
(45) Date of Patent: Nov. 7, 2017

(54) PHARMACEUTICAL COMPOSITIONS AND METHODS FOR ENHANCING TARGETING OF THERAPEUTIC COMPOUNDS TO THE CENTRAL NERVOUS SYSTEM

(75) Inventors: William H. Frey, II, White Bear Lake, MN (US); Leah Ranae Bresin Hanson, Vadnais Heights, MN (US); Shyeilla V. Dhuria, Minneapolis, MN (US)

(73) Assignee: HealthPartners Research Foundation, Bloomington, MN (US)

( * ) Notice: Subject to any disclaimer, the term of this patent is extended or adjusted under 35 U.S.C. 154(b) by 8 days.

(21) Appl. No.: 12/134,385

(22) Filed: Jun. 6, 2008

(65) Prior Publication Data
US 2008/0305077 A1  Dec. 11, 2008

Related U.S. Application Data

(60) Provisional application No. 60/942,696, filed on Jun. 8, 2007.

(51) Int. Cl.
| *A61K 38/20* | (2006.01) |
| *A61K 9/00* | (2006.01) |
| *A61K 31/16* | (2006.01) |
| *A61K 33/24* | (2006.01) |
| *A61K 38/18* | (2006.01) |
| *A61K 38/19* | (2006.01) |
| *A61K 38/28* | (2006.01) |
| *A61K 38/30* | (2006.01) |
| *A61K 45/06* | (2006.01) |

(52) U.S. Cl.
CPC ........ *A61K 38/2006* (2013.01); *A61K 9/0043* (2013.01); *A61K 31/16* (2013.01); *A61K 33/24* (2013.01); *A61K 38/1841* (2013.01); *A61K 38/191* (2013.01); *A61K 38/28* (2013.01); *A61K 38/30* (2013.01); *A61K 45/06* (2013.01)

(58) Field of Classification Search
None
See application file for complete search history.

(56) References Cited

U.S. PATENT DOCUMENTS

| 2,989,437 | A | 6/1961 | Wruble | |
| 6,180,603 | B1 * | 1/2001 | Frey, II | 514/12 |
| 7,071,172 | B2 | 7/2006 | McCown et al. | |
| 7,112,566 | B1 * | 9/2006 | Siegel et al. | 514/12 |
| 2001/0053775 | A1 * | 12/2001 | Seidel et al. | 514/179 |
| 2002/0141971 | A1 * | 10/2002 | Frey, II | 424/85.1 |
| 2003/0229025 | A1 | 12/2003 | Xiao et al. | |
| 2006/0039995 | A1 * | 2/2006 | Frey et al. | 424/646 |
| 2007/0021331 | A1 | 1/2007 | Fraser et al. | |
| 2007/0054843 | A1 | 3/2007 | Yeomans et al. | |
| 2007/0086942 | A1 | 4/2007 | Chang et al. | |
| 2007/0092500 | A1 | 4/2007 | Frey, II et al. | |
| 2007/0093420 | A1 | 4/2007 | Yeomans et al. | |

FOREIGN PATENT DOCUMENTS

| JP | 2009-506071 | 2/2009 |
| JP | 2009-506076 | 2/2009 |
| WO | WO98/42275 | 10/1998 |
| WO | WO2007/025249 | 3/2007 |
| WO | WO2007/025286 | 3/2007 |

OTHER PUBLICATIONS

Järvinen K and Uritti A. Duration and long-term efficacy of phenylephrine-induced reduction in the systemic absorption of ophthalmic timolol in rabbits. J Ocul. Pharmacol. 1992; 8(2):91-98; abstract only.*
Vachharajani NN et al. A pharmacokinetic interactioni study between butorphanol and sumatriptan nasal sprays in healthy subjects: importance of the timing of butorphanol administration. Cephalalgia, 2002; 22:282-287.*
Neuber et al. 2008 "neurodegeneration and motor dysfunction in a conditional model of Parkinson's disease" J Neurosci 28(10):2471-2484.*
Rafii and Aisen 2010 "Recent developments in Alzheimer's disease therapeutics" BMC Medicine 7:7.*
Jarvinen 1992 "Duration and long-term efficacy of phenyephrine-induced reduction in the systemic absorption of ophthalmic timolol in rabbits" J Ocular Pharma 8(2):91-98.*
S. Telegaonkar, P. R. Mishra, Intranasal delivery: An approach to bypass the blood brain barrier, Indian J. Phermacol, Jun. 2004, vol. 36, Issue 3 140-147.
T.M. Ross et al., Intranasal administration of interferon beta bypasses the blood-brain barrier to target the central nervous system and cervical lymph nodes: a non-invasive treatment strategy for multiple sclerosis, Journal of Neuroimmunology, 151 (2004) 66-77.
Leah R. Hanson, William H. Frey II, Strategies for Intranasal Delivery of therapeutics for the Prevention and Treatment of NeuroAIDS, J. Neuroimmune Pharm (2007) 2:81-86.

(Continued)

*Primary Examiner* — Adam Weidner
(74) *Attorney, Agent, or Firm* — Barnes & Thornburg LLP; Jeffrey R. Stone

(57) ABSTRACT

Pharmaceutical compositions and methods for enhancing targeting of therapeutic compounds to, inter alia, the CNS applied via intranasal administration while reducing non-target exposure are provided. In certain embodiments, at least one vasoconstrictor is provided intranasally prior to intranasal administration of at least one therapeutic compound. In other embodiments, the vasoconstrictor(s) and therapeutic compound(s) are combined in a pharmaceutical composition and delivered intranasally. The present invention substantially increases targeting of the therapeutic compound(s) to, inter alia, the CNS while substantially reducing unwanted and potentially harmful systemic exposure. The preferred administration of the invention applies the vasoconstrictor(s) and/or therapeutic compound(s) to the upper third of the nasal cavity, though application to the lower two-thirds of the nasal cavity is also within the scope of the invention.

16 Claims, 5 Drawing Sheets

(56) References Cited

OTHER PUBLICATIONS

Talegaonkar S.;Mishra P.R.: "Intranasal delivery: An approach to bypass the blood brain barrier", Indian Journal of Pharmacology, vol. 36, No. 3, Jun. 2004 (Jun. 2004), pp. 140-147, XP002672376, ISSN: 0253-7613.
Charlton S.T.; David S.S.; Illum L.: "Evaluation of effect of ephedrine on the transport of drugs from the nasal cavity to the systemic circulation and the central nervous system", Journal of Drug Targeting, vol. 15, No. 5, May 31, 2007 (May 31, 2007), pp. 370-377, XP9157742, ISSN: 1061-186X, DOI: DOI:10, 1080/ 10611860701393370.

\* cited by examiner

FIGURE 1: BLOOD CONCENTRATION OF HC FOLLOWING DIFFERENT PRETREATMENT TIME INTERVALS
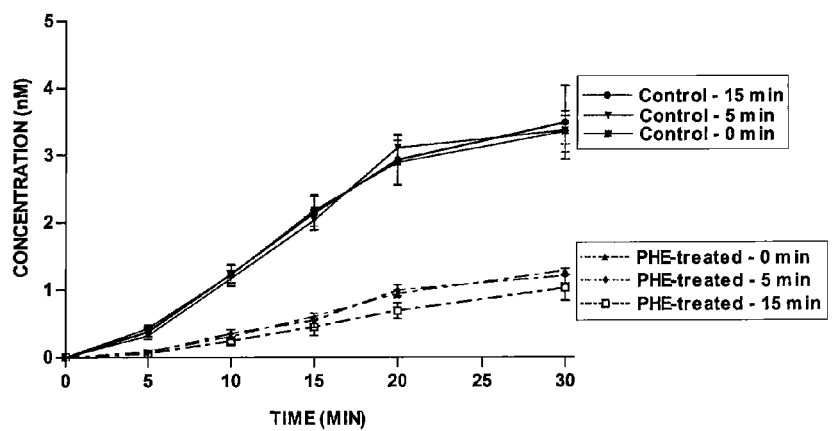
FIGURE 2: BLOOD CONCENTRATION OF HC AFTER MERGING PRETREATMENT TIME INTERVAL DATA
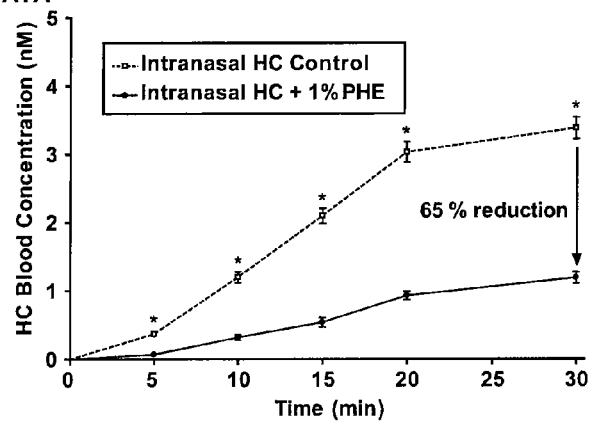

FIGURE 3: CNS TISSUE-TO-BLOOD CONCENTRATION RATIOS OF HC FOLLOWING INTRANASAL ADMINISTRATION IN THE PRESENCE AND ABSENCE OF 1% PHE

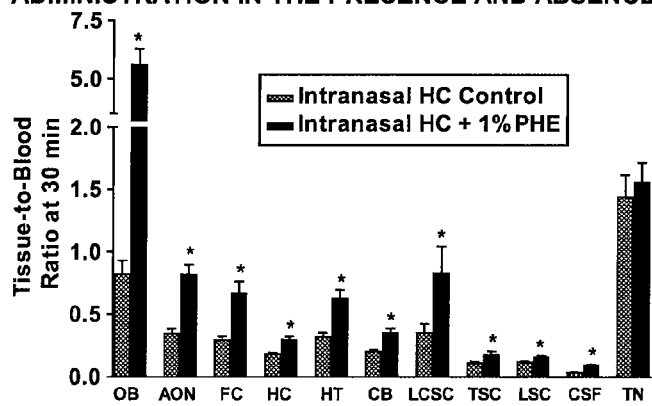

OB = olfactory bulbs, AON = anterior olfactory nucleus, FC = frontal cortex, HC = hippocampus, HT = hypothalamus, CB = cerebellum, LCSC = lower cervical spinal cord, TSC = thoracic spinal cord, CSF = cerebrospinal fluid, TN = trigeminal nerve FIGURE 4: BLOOD CONCENTRATION OF TP FOLLOWING INTRANASAL ADMINISTRATION IN THE PRESENCE AND ABSENCE OF 1% PHE
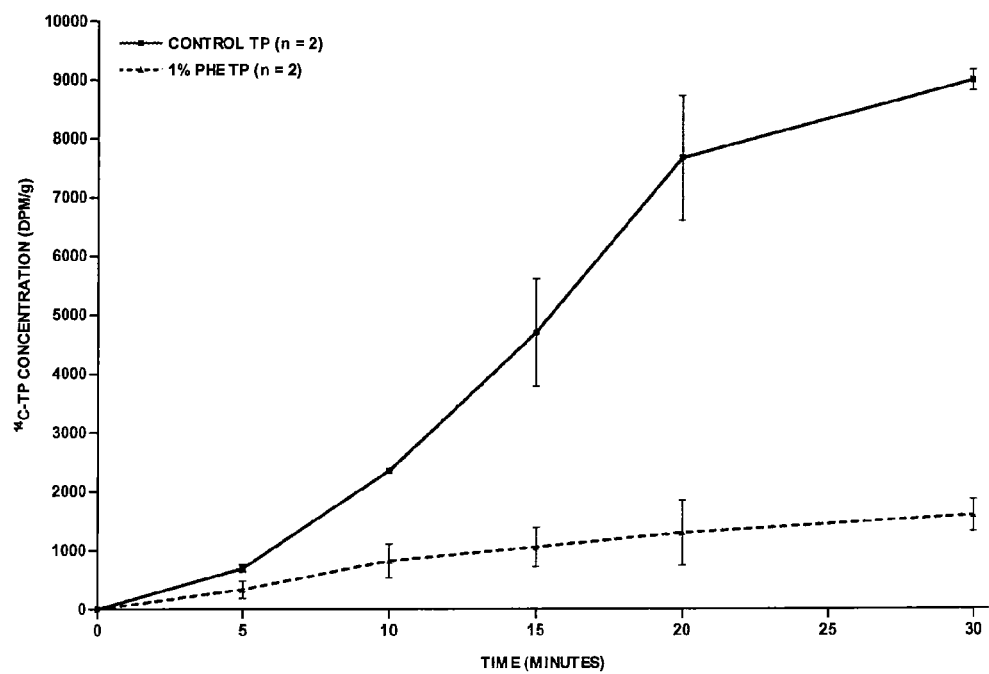

FIGURE 5: CONCENTRATIONS OF TP IN PERIPHERAL TISSUES IN THE PRESENCE AND ABSENCE OF 1% PHE
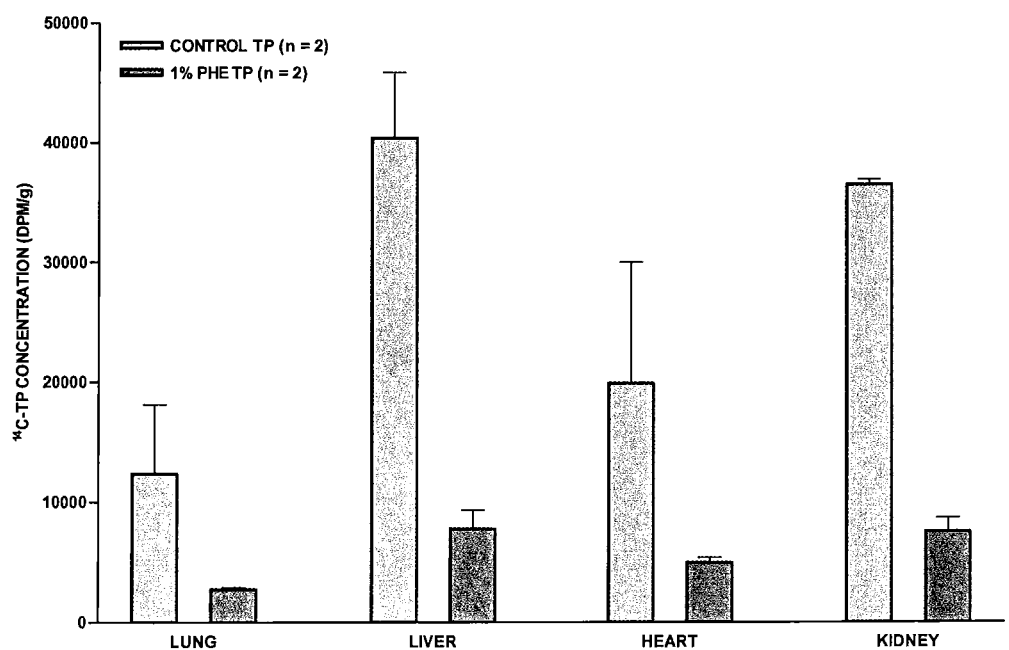

FIGURE 6: BLOOD CONCENTRATION OF KTP FOLLOWING INTRAVENOUS ADMINISTRATION AND INTRANASAL ADMINISTRATION IN THE PRESENCE AND ABSENCE OF PHE

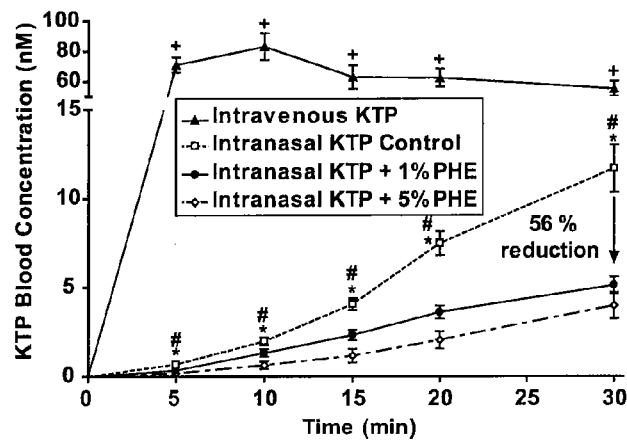

FIGURE 7: CNS TISSUE-TO-BLOOD CONCENTRATION RATIOS OF KTP FOLLOWING INTRAVENOUS ADMINISTRATION AND INTRANASAL ADMINISTRATION IN THE PRESENCE AND ABSENCE OF PHE

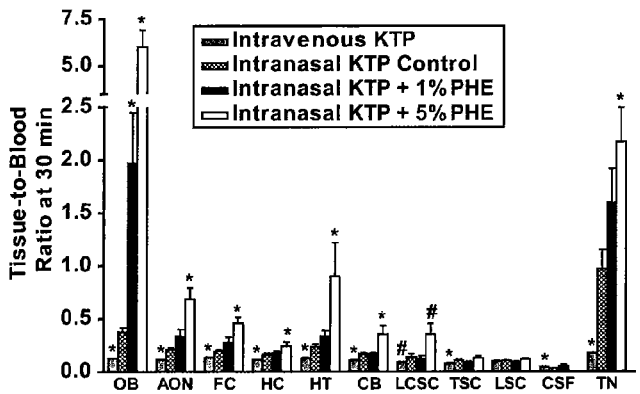

OB = olfactory bulbs, AON = anterior olfactory nucleus, FC = frontal cortex, HC = hippocampus, HT = hypothalamus, CB = cerebellum, LCSC = lower cervical spinal cord, TSC = thoracic spinal cord, CSF = cerebrospinal fluid, TN = trigeminal nerve

PHARMACEUTICAL COMPOSITIONS AND METHODS FOR ENHANCING TARGETING OF THERAPEUTIC COMPOUNDS TO THE CENTRAL NERVOUS SYSTEM

CROSS-REFERENCE TO RELATED APPLICATIONS

The present application claims priority to provisional application No. 60/942,696, filed on Jun. 8, 2007 under the same title, the entire contents of which are incorporated herein by reference.

BACKGROUND OF THE INVENTION

Field of the Invention

The present invention is directed to pharmaceutical compositions and methods for reducing systemic absorption of therapeutic compounds while enhancing targeting of such compounds or agents to, inter alia, the central nervous system (CNS) via intranasal administration. More specifically, use of vasoconstrictors as a pretreatment or in a pharmaceutical composition with therapeutic(s), delivered intranasally, to increase targeting to, inter alia, the CNS while limiting systemic exposure.

Description of the Related Art

It is known that intranasal administration of therapeutic compounds or agents may, in some cases, increase the effectiveness of certain therapeutic compounds or agents in bypassing the blood brain barrier (BBB) and delivering the compound or agent directly to the CNS. Thus, intranasal administration of therapeutic compounds may allow increased prevention and/or treatment of certain diseases or conditions.

It is also known that greater than 98% of small molecule and nearly 100% of large molecule CNS drugs developed by the pharmaceutical industry do not cross the BBB. Intracerebroventricular or intraparenchymal drug administration can directly deliver therapeutics to the brain; however, these methods are invasive, inconvenient, and impractical for the numbers of individuals requiring therapeutic interventions for treating CNS disorders. Intranasal drug administration is a non-invasive and convenient means to rapidly target therapeutics of varying physical and chemical properties to the CNS. The olfactory and trigeminal neural pathways connecting the nasal passages to the CNS are clearly involved in the delivery of therapeutic compounds applied via intranasal administration to the upper third of the nasal cavity. In addition to these neural pathways, perivascular pathways, and pathways involving the cerebrospinal fluid or nasal lymphatics may play a central role in the distribution of therapeutics from the nasal cavity to the CNS. Numerous therapeutics have been delivered to the CNS following intranasal administration, to both the upper third and lower two-thirds of the nasal cavity, and have demonstrated pharmacological effects in animals and in humans.

The intranasal method of drug delivery holds great promise as an alternative to more invasive routes, however, a number of factors limit the efficiency of intranasal delivery to the CNS. Absorption of intranasally applied drugs into the capillary network in the nasal mucosa can decrease the amount of drug available for direct transport into the CNS. Additional factors within the nasal cavity, including the presence of nasal mucociliary clearance mechanisms, metabolizing enzymes, efflux transporters and nasal congestion can also reduce the efficiency of delivery into the CNS. In particular, therapeutic compounds may be absorbed into the blood and/or delivered to peripheral (non-target) tissues, thus reducing delivery of the compound to the target. As a result, the efficacy of administering therapeutic compounds to the lower two-thirds of the nasal cavity with the goal of delivering therapeutics to the CNS is greatly diminished. Further, the efficacy of administering therapeutic compounds to the upper one-third of the nasal cavity as a means to target therapeutics to the CNS could be improved.

It would be desirable to reduce absorption of intranasally-administered therapeutic compounds or agents into the blood and delivery to non-target or peripheral tissues. It would be further desirable to increase deposition and delivery of the therapeutic compounds or agents to, inter alia, the CNS, e.g., within the olfactory epithelium, the olfactory bulbs as well as the lymphatic system, and it would be desirable to increase therapeutic compound targeting relative to the blood to the frontal cortex, anterior olfactory nucleus, hippocampus, hypothalamus, pons, midbrain, medulla, cerebellum and to the meninges. It would be further desirable to provide an intranasal delivery method and pharmaceutical composition(s) that are effective and efficient in facilitating delivery of therapeutic compounds to the CNS, regardless of whether the therapeutic composition is delivered to the upper one-third or lower two-thirds of the nasal cavity.

The present invention addresses, inter alia, these issues.

BRIEF SUMMARY OF THE INVENTION

Pharmaceutical compositions and methods for enhancing targeting of therapeutic compounds to the CNS applied via intranasal administration while reducing non-target exposure are provided. In certain embodiments, at least one vasoconstrictor is provided intranasally prior to intranasal administration of at least one therapeutic compound. In other embodiments, the vasoconstrictor(s) and therapeutic compound(s) are combined in a pharmaceutical composition and delivered intranasally. The present invention substantially increases targeting of the therapeutic compound(s) to the CNS while substantially reducing unwanted and potentially harmful systemic exposure. The preferred administration of the invention applies the vasoconstrictor(s) and/or therapeutic compound(s) to the upper third of the nasal cavity, though application to the lower two-thirds of the nasal cavity is also within the scope of the invention.

An object of the present invention comprises providing methods and/or pharmaceutical compositions to increase targeted delivery and efficiency thereof of therapeutic compositions to, inter alia, the CNS, lymphatics and meninges via intranasal administration.

Another object of the present invention comprises providing methods and/or pharmaceutical compositions to reduce systemic exposure, or exposure to non-target or peripheral tissues, to therapeutic compositions administered intranasally.

Another object of the present invention comprises providing methods and/or pharmaceutical compositions to increase efficacy of therapeutic compound targeting to, inter alia, the CNS, lymphatics and meninges.

Another object of the present invention comprises methods and/or pharmaceutical compositions to increase efficacy of application of therapeutic compounds to the olfactory epithelium, olfactory bulbs and/or anterior olfactory nucleus for treatment of anosmia, a condition associated with Alzheimer's disease, Parkinson's disease, other neurodegenerative disorders and normal aging.

Another object of the present invention comprises methods and/or pharmaceutical compositions to increase efficacy of application of therapeutic compounds to the frontal cortex to reach brain targets involved in frontotemporal dementia, personality disorders, cognition disorders, motor dysfunction and Alzheimer's disease.

Another object of the present invention comprises methods and/or pharmaceutical compositions to increase efficacy of application of therapeutic compounds to the hippocampus for the treatment of learning and memory disorders associated with Alzheimer's disease and other neurologic disorders.

Another object of the present invention comprises methods and/or pharmaceutical compositions to increase efficacy of application of therapeutic compounds to reach the cerebellum and brainstem for treating ataxia, Parkinson's disease and other motor disorders.

Another object of the present invention comprises methods and/or pharmaceutical compositions to increase efficacy of application of therapeutic compounds to reach the lymphatic system to treat or prevent brain tumors, multiple myeloma, Hodgkin's disease, lymphadenitis, lymphatic filariasis, lymphoma, non-Hodgkin's lymphoma, thumus cancer and other forms of cancer, AIDS, neuroAIDS, SCID, autoimmune diseases, Sjogren's syndrome, chronic sinusitis, allergies, lupus and/or multiple sclerosis.

Another object of the present invention comprises methods and/or pharmaceutical compositions to increase efficacy of application of therapeutic compounds, including but not limited to potent antibiotics and/or antiviral medications, to the meninges surrounding the brain for treatment of meningitis and/or encephalitis.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying Figures and Tables included herein.

FIG. 1 is a graph illustrating blood concentration of HC following different pretreatment time intervals;

FIG. 2 is a graph illustrating blood concentration of the HC after merging pretreatment time interval data;

FIG. 3 is a graph illustrating CAN tissue-to-blood concentration ratios of HC following intranasal administration in the presence and absence of 1% PHE;

FIG. 4 is a graph illustrating blood concentration of TP following intranasal administration in the presence and absence of 1% PHE;

FIG. 5 is a graph illustrating concentrations of TP in peripheral tissues in the presence and absence of 1% PHE;

FIG. 6 is a graph illustrating blood concentration of KTP following intravenous administration and intranasal administration in the presence and absence of PHE; and FIG. 7 is a graph illustrating TNS tissue-to-blood concentration ratios of KTP following intravenous administration and intranasal administration in the presence and absence of PHE.

DETAILED DESCRIPTION OF THE INVENTION, INCLUDING THE BEST MODE

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

Definitions

As used herein, "central nervous system" (CNS) refers to the brain and spinal cord and associated tissues.

As used herein, "drug targeting" refers to increasing drug concentration in a tissue relative to the concentration of that drug in the blood.

As used herein, "efficiency" refers to targeting specificity of the drug, i.e., therapeutic compound to a particular physiological location, delivery with minimal residual loss to non-target physiological locations, or both.

As used herein, "meninges" refers to the dura, pia and arachnoid membranes surrounding the brain and spinal cord.

As used herein, "brainstem" refers to the pons, medulla and midbrain.

An "effective amount" of therapeutic compound or agent is an amount sufficient to prevent, treat, reduce and/or ameliorate the symptoms, neuronal damage and/or underlying causes of any of the referenced disorders or diseases. In some instances, an "effective amount" is sufficient to eliminate the symptoms of those diseases and, perhaps, overcome the disease itself.

In the context of the present invention, the terms "treat" and "therapy" and "therapeutic" and the like refer to alleviate, slow the progression, prophylaxis, attenuation or cure of cerebral ischemia or neurodegeneration or other CNS-related disease and/or condition.

"Prevent", as used herein, refers to putting off, delaying, slowing, inhibiting, or otherwise stopping, reducing or ameliorating the onset of cerebral ischemia or neurodegeneration or other CNS-related disease and/or condition. It is preferred that a large enough quantity of the agent be applied in non-toxic levels in order to provide an effective level of neuroprotection. The method of the present invention may be used with any animal, such as a mammal or a bird (avian), more preferably a mammal. Poultry are a preferred bird. Exemplary mammals include, but are not limited to rats, cats, dogs, horses, cows, sheep, pigs, and more preferably humans.

"Intranasal Delivery" as used herein, refers to the application, delivery and/or administration of at least one therapeutic agent or compound, at least one vasoconstrictor and/or a combination thereof, i.e., pharmaceutical composition, to the nasal cavity of the subject. Such intranasal delivery comprises application, delivery and/or administration of the compound(s), vasoconstrictor(s) and/or pharmaceutical composition to the entire nasal cavity, the upper one-third of the nasal cavity and/or the lower two-thirds of the nasal cavity.

Intranasal delivery is a method to target drugs to the CNS for the treatment and/or prevention of neurologic and psychiatric diseases and disorders. It is known that a wide variety of drugs rapidly reach the brain and spinal cord and have beneficial effects in animals and in humans after intranasal administration. The present invention enhances intranasal therapeutic compound delivery to, inter alia, the olfactory epithelium, olfactory bulbs and lymphatics and enhances drug targeting to the olfactory epithelium, CNS, meninges and lymphatics by incorporating a vasoconstrictor into the nasal formulation and/or by applying a vasoconstrictor as a pretreatment to the intranasal application of the therapeutic compound. Thus, intranasal delivery of a therapeutic compound in combination with an agent that constricts blood vessels (i.e. a vasoconstrictor) within and around the nasal mucosa and nasal epithelium enhances intranasal drug targeting to the CNS, meninges and lymphatics by reducing absorption into the blood, increasing concentrations in selected regions of the CNS and in lymphatics, or both. Constriction of blood vessels resulting from action of the vasoconstrictor in the nasal cavity may facilitate transport into the brain along olfactory and trigeminal neural pathways, perivascular pathways, or lymphatic pathways. Use of vasoconstrictors in a pharmaceutical composition with therapeutics, delivered intranasally, was not found to increase delivery of therapeutics to all regions of the central nervous system. For example, delivery was not increased to the hippocampus, pons, cerebellum or the trigeminal nerve.

The method of the present invention delivers, administers and/or applies the therapeutic compound, vasoconstrictor and/or pharmaceutical composition to the nasal cavity of a mammal. It is preferred that the therapeutic compound, vasoconstrictor and/or pharmaceutical composition be delivered to the olfactory neuroepithelium in order to promote rapid and efficient delivery of the therapeutic compound, vasoconstrictor and/or pharmaceutical composition to the CNS along the olfactory neural pathway and to the respiratory and olfactory epithelium to promote rapid and efficient delivery of the therapeutic compound, vasoconstrictor and/or pharmaceutical composition to the CNS along the trigeminal neural pathway rather than into the capillaries within the nasal epithelium. Transport of the therapeutic compound, vasoconstrictor and/or pharmaceutical composition to the brain by means of the olfactory and trigeminal neural pathways rather than the circulatory system is preferred so that harmful systemic side effects and potentially short half-life of the therapeutic agent in the blood are avoided. The preferred method allows direct delivery of various embodiments of the present invention to the CNS and to the meninges and lymphatics. However, as discussed above, the present invention is not limited to intranasal delivery to the upper third of the nasal cavity, therefore, in certain embodiments, the therapeutic compound, vasoconstrictor and/or pharmaceutical composition of the present invention may be delivered to the lower two-thirds of the nasal cavity.

To deliver the therapeutic compound to, inter alia, the CNS, vasoconstrictor and/or pharmaceutical composition to the CNS, at least one therapeutic compound, and/or at least one therapeutic compound in combination with at least one vasoconstrictor as a pharmaceutical composition, and/or using the vasoconstrictor(s) as a pretreatment, may be administered to the nasal cavity, either the lower two-thirds and/or the upper third thereof. If applied to the upper third of the nasal cavity, the vasoconstrictor and/or therapeutic compound comprising in certain embodiments a pharmaceutical composition of the present invention, is applied to the respiratory epithelium of the nasal cavity or to the olfactory epithelium located in the upper one-third of the nasal cavity. In all cases of application and/or administration, the composition may be administered intranasally as a powder or liquid spray, nose drops, a gel, lipid emulsion, lipid nanoparticles, lipid nanospheres or ointment, through a tube or catheter, by syringe, packtail, pledget or by submucosal infusion.

The optimal concentration of the active therapeutic agent, i.e., therapeutic compound, as well as the concentration of the vasoconstrictor, will necessarily depend upon the specific neurologic agent used, the characteristics of the patient and the nature of the disease or condition for which the agent is being used, though an effective amount is contemplated. In addition, the concentration will depend upon whether the agent is being employed in a preventive or treatment capacity. Further, the stage of a particular disease or disorder, e.g., early vs. late Alzheimer's disease, may dictate the optimal concentration of the therapeutic compound.

The present invention enhances intranasal therapeutic compound targeting to the CNS by incorporating a vasoconstrictor into the nasal formulation. Constriction of blood vessels resulting from action of the vasoconstrictor in the nasal cavity facilitates transport of the therapeutic compound(s) or agent(s) into the brain along olfactory and trigeminal neural pathways, perivascular pathways, or lymphatic pathways. Thus, intranasal delivery of a therapeutic compound(s) or agent(s) in combination with an agent that constricts blood vessels (i.e. a vasoconstrictor) within or in the proximity of the mucosa of the nasal cavity enhances intranasal drug targeting to, inter alia, the CNS by reducing absorption into the blood, increasing CNS concentrations (as well as other targeted locations), or both.

Exemplary work performed according to one embodiment of the inventive method was performed as follows.

Exemplary Experiment and Data Set 1

Methods

We investigated whether incorporation of a vasoconstrictor (phenylephrine, PHE) in the nasal formulation enhances drug targeting of an intranasally applied neuropeptide (hypocretin-1, HC) to the brain in rodents. Several factors may effect CNS concentrations of HC following intranasal administration of HC in the presence of PHE, including the dose of vasoconstrictor, the time after intranasal delivery, and the pretreatment time interval. PHE is commonly used at a dose of 1% for nasal decongestion and topical nasal application of PHE results in a rapid onset of action and duration of action of approximately 4 hours. Ideally, it would be preferred to have a nasal formulation where the vasoconstrictor and CNS drug are administered together, without the need for pretreatment of the nasal cavity with vasoconstrictor. Clearly this would be more convenient than having to intranasally pretreat, wait a period of time (5 min or 15 min), and then intranasally administer the CNS drug with additional vasoconstrictor. However, waiting a short period of time may be a necessary step to allow the vasoconstrictor to activate adrenergic receptors located on blood vessels in the nasal cavity to result in constriction. Thus, in these experiments, three pretreatment time intervals were investigated: 0 min (or no pretreatment), 5 min, 15 min, to determine the time interval necessary to wait to allow the intranasally applied 1% PHE to take effect. Anesthetized rats were sacrificed at 30 minutes following intranasal delivery of HC and 1% PHE, since typically high brain concentrations are achieved within 25-30 minutes of intranasal administration.

Results & Discussion

Data Analysis

In order to determine if the pretreatment time interval had an effect on intranasal delivery to the CNS, one-way ANOVAs comparing tissue concentrations in the three groups (0 min, 5 min, 15 min) from the control animals were performed. One-way ANOVAs comparing tissue concentrations in the three groups from the PHE-treated animals were also performed. These statistical analyses demonstrated that the pretreatment time interval did not significantly affect intranasal delivery of HC to most CNS and peripheral tissues at the 30 minute sacrifice time point. Stated differently, the data demonstrate no therapeutic advantage from pretreatment with a vasoconstrictor. Thus, the therapeutic compound(s) and vasoconstrictor(s) may be combined in a pharmaceutic composition while retaining full therapeutic benefit of the present invention. Certain tissues such as the trigeminal nerve, superficial cervical lymph nodes, deep cervical lymph nodes, and dorsal and ventral meninges, were found to be statistically different from the other groups, however, these differences may be artifactual, since the majority of other tissues were unaffected by the pretreatment time interval. Pretreatment time interval also did not significantly affect delivery into the blood over the time course of the intranasal delivery experiments (FIG. 1). As a result, data obtained from control animals with different pretreatment time intervals were merged and data obtained from PHE-treated animals with different pretreatment time intervals were merged. Statistical comparisons were made between tissue concentrations in control animals (n=28) and PHE-treated animals (n=23).

Effect of 1% PHE on Site of Intranasal Administration (Blood, Nasal Epithelia, and Lymphatics)

Incorporation of 1% PHE into the nasal formulation significantly reduced absorption of HC into the blood (65% reduction) (FIG. 2), while significantly increasing concentrations in the olfactory epithelium (Table 1). It was also observed that 1% PHE significantly reduced concentrations in the respiratory epithelium compared to controls, as well as in the trigeminal nerve, which innervates the lateral walls and anterior portion of the nasal mucosa, in close relation to the respiratory epithelium (Table 1). Delivery to the nasal lymphatics was also significantly increased with 1% PHE, as observed by the increased concentration of HC in the superficial cervical lymph nodes and deep cervical lymph nodes (Table 1).

These results demonstrated significantly greater delivery of HC to the olfactory epithelium in the presence of 1% PHE. Thus, use of a vasoconstrictor is an alternative to expensive nasal delivery devices claiming to target therapeutics to the olfactory region of the nasal cavity. The increased deposition in the olfactory epithelium may be due to reduced clearance of the drug into the blood, thereby increasing the residence time of the formulation in the nasal cavity. Interestingly, these results also showed that delivery to the respiratory epithelium was significantly reduced compared to controls when vasoconstrictor was included in the nasal formulation. The respiratory mucosa, like the olfactory mucosa, is covered by a dense network of blood vessels. It was thought that the respiratory epithelium would also have a greater HC concentration in the PHE-treated animals compared to controls due to the reduced clearance of HC into the blood vessels in the respiratory mucosa. It is possible that in addition to reducing clearance of the drug into the blood and increasing the residence time in the nasal cavity, the vasoconstrictor opens up nasal passages due to its decongestant effects and allows more of the intranasally administered HC to reach the olfactory epithelium, and reduces the contact with the respiratory epithelium.

The blood concentration is significantly reduced in the presence of vasoconstrictor, so we would expect that the total nasal cavity concentration should be increased in PHE-treated animals compared to controls. When one looks at the total nasal cavity concentration, the concentration of HC is the same for the control and PHE-treated groups (24,162 vs. 24,787 nM); the difference is in the relative distribution of the drug within the nasal epithelia. Thus, it is more likely that the latter mechanism is primarily responsible for the increased deposition in the olfactory epithelium. It is possible that rather than staying in the nasal cavity, the therapeutic compound is channeled into the nasal lymphatics. In fact, concentrations in the superficial cervical lymph nodes and deep cervical lymph nodes, which are linked to the nasal cavity through lymphatic channels, were significantly increased in the presence of vasoconstrictor (Table 1). In summary, these results indicate that inclusion of a vasoconstrictor results in increased delivery to the olfactory epithelium and this is primarily due to the opening of the nasal passages, while increased delivery to the lymph nodes is primarily due to reduced clearance of the drug into the blood from the nasal cavity.

Effect of 1% PHE on Intranasal Delivery to the Brain and Lymphatics

Intranasal delivery of HC to the brain was affected by 1% PHE in the nasal formulation. HC concentrations in the olfactory bulbs doubled in the presence of 1% PHE, from 2.7 nM to 5.6 nM ($p<0.05$), likely due to the high concentration gradient present in the olfactory epithelium (Table 1). Delivery to other rostral brain regions, such as the anterior olfactory nucleus and frontal cortex, was unaffected by 1% PHE, though concentrations were slightly reduced (Table 1). It is possible that there was not enough time for the drug to diffuse to these regions and increased concentrations may have been achieved if animals were sacrificed at later times (i.e. at 60 or 120 minutes). Regions in the middle of the brain, including the hippocampus and hypothalamus, had significantly reduced concentrations of HC (Table 1). Moving to the caudal portions of the brain, such as the brainstem and cerebellum, it was found that concentrations were reduced (Table 1).

These data demonstrate that intranasal delivery to the rostral portion of the brain via the olfactory nerves is more dependent on the olfactory epithelium concentration than on the blood. The main driving force for absorption into the rostral brain is the high concentration gradient present in the olfactory epithelium, and as a result, a significant increase in olfactory bulb concentration was observed in PHE-treated animals. Results from these experiments also suggest an important role of the vasculature and/or the trigeminal nerve in intranasal delivery to middle and caudal brain regions, since significantly reducing blood concentrations also resulted in significantly reduced trigeminal nerve and brain concentrations. Trigeminal nerve and blood concentrations were linked: a 2.8-fold reduction in blood concentration resulted in a reduction in trigeminal nerve concentration of HC of the same magnitude Effect of 1% PHE on Delivery to Peripheral Tissue/Systemic Delivery With regard to exposure in peripheral tissues, intranasal delivery of HC with 1% PHE significantly reduced HC concentrations in the spleen and heart, while delivery to the liver and kidneys was unchanged in the presence of 1% PHE (Table 1). For therapeutic compounds, e.g., drugs, that have adverse side effects due to widespread distribution in the body via the systemic circulation, vasoconstrictors in intranasal formulations may be a strategy to reduce systemic side effects due to the reduction in delivery to peripheral tissues and to the blood.

Effect of 1% PHE on Intranasal Drug Targeting to the CNS, Lymphatics, and Meninges Normalizing tissue concentrations to blood concentrations at 30 minutes provides an assessment of drug targeting to the tissue relative to the blood and allows for direct comparison between the control and PHE-treated groups (FIG. 3). Therapeutic compound targeting to nearly all CNS regions was significantly increased ($p<0.05$), with the greatest drug targeting to the rostral brain tissues such as the olfactory bulbs (6.8-fold), anterior olfactory nucleus (2.4-fold), and frontal cortex (2.3-fold) (FIG. 3). Therapeutic compound targeting to caudal brain tissues including the midbrain, medulla and cerebellum (1.7-fold) was increased compared to the control animals, (FIG. 3). Although delivery to the trigeminal nerve was reduced, as evidenced by lower concentrations with 1% PHE, drug targeting to the trigeminal nerve was not significantly different between control and PHE-treated groups (FIG. 3).

These results show that although absolute concentrations in the brain (excluding the olfactory bulbs) were reduced in the presence of a vasoconstrictor, blood concentrations were also significantly reduced, with the end result of increased intranasal therapeutic compound targeting to the brain. These results demonstrate that use of vasoconstrictors in intranasal formulations may be extremely valuable for targeting potent therapeutic compounds to the CNS, while reducing absorption into blood and widespread distribution to the rest of the body. For therapeutic compounds that are active at nanomolar concentrations, the reduction in brain concentrations should not significantly diminish the desired therapeutic response. For therapeutic compounds that have adverse effects in the blood or peripheral tissues, vasoconstrictors may be useful in preventing the drug from distributing to non-target sites where they can cause side effects. For therapeutic compounds that are extensively bound by plasma proteins or for biologics that are rapidly degraded by plasma proteases or drug metabolizing organs, vasoconstrictors can increase the availability of free and intact drug for absorption into the CNS.

The superficial and deep cervical lymph nodes were also significantly targeted with 1% PHE in the nasal formulation (5.7-fold increase for both, data not shown), which may be important for targeting immunotherapeutics to the lymphatic system. HC targeting after intranasal administration was also increased to the meninges (2.9-fold for ventral meninges, 1.7-fold for dorsal meninges) surrounding the brain, which could have therapeutic potential for targeting drugs to the meninges for the treatment of meningitis or encephalitis (data not shown). The fact that tissue-to-blood ratios were either increased or unchanged in CNS tissues, lymphatic tissues, and the meninges in the presence of 1% PHE suggests that incorporation of a vasoconstrictor into nasal formulations can improve drug targeting, and minimize targeting to the blood, which may be valuable for potent drugs that are accompanied by intolerable side effects in the blood and/or peripheral tissues.

Conclusion for Exemplary Experiment and Data Set 1

Incorporation of at least one vasoconstrictor in a nasal formulation including at least one therapeutic compound, i.e., a pharmaceutical composition, enhances intranasal therapeutic compounds targeting of therapeutics to, inter alia, the CNS, meninges and lymphatics by reducing absorption into the blood, increasing concentrations in, inter alia, the CNS, or both. Results from these experiments demonstrate that inclusion of a vasoconstrictor significantly enhances therapeutic compound delivery to the olfactory epithelium, olfactory bulbs and lymphatics and significantly enhances therapeutic compounds targeting to, inter alia, the CNS, meninges and lymphatics relative to blood following intranasal administration. In previous experiments comparing intravenous (IV) to intranasal (IN) delivery of HC in the absence of any additives, intranasal HC significantly targeted HC to the brain (Table 2, IN vs. IV). Inclusion of a vasoconstrictor in the intranasal formulation (IN PHE) further enhances brain targeting of HC compared to the intravenous delivery from the previous study (Table 2, IN PHE vs. IV). In addition, compared to intranasal delivery with no additives, intranasal administration of HC in combination with 1% PHE further enhances intranasal drug targeting to the brain, with increased targeting to the olfactory bulbs (7-fold increase), anterior olfactory nucleus (2-fold increase), frontal cortex (2-fold increase), hippocampus (2-fold increase), and hypothalamus (2-fold increase) (Table 2, IN PHE vs. IN). 1% PHE also enhances intranasal drug targeting to the superficial and deep cervical lymph nodes (5 to 6-fold) and to the meninges surrounding the brain (2-fold). Therefore, inclusion of a vasoconstrictor in an intranasal formulation is a novel strategy to further enhance intranasal drug targeting to the brain and lymphatics compared to other routes of administration. In addition, inclusion of a vasoconstrictor in the formulation is a novel strategy to selectively increase drug delivery to the olfactory epithelium, lymphatics and certain regions of the CNS including the olfactory bulbs without increasing delivery to other regions of the CNS including the hippocampus, pons, cerebellum or the trigeminal nerve.

Exemplary Experiment and Data Set 2

The vasoconstrictors selected for these experiments were tetrahydrozoline (THZ, MW 200), an imidazoline derivative, and phenylephrine (PHE, MW 204), an arylalkylamine derivative. Both vasoconstricting agents are α-adrenergic agonists with short duration of action (4-6 hours). The therapeutic compound selected was hypocretin-1 (HC, MW 3500), a peptide with therapeutic potential for treating narcolepsy. In addition to determining the effect of vasoconstrictors on the intranasal delivery of hypocretin-1 to the CNS, peripheral tissues and blood, vasoconstrictor effects on the drug targeting index (DTI) were also examined.

Methods

Studies of intranasal delivery of $^{125}$I-HC in the presence or absence of THZ or PHE to the CNS, peripheral tissues and blood were conducted in anesthetized adult male Sprague-Dawley rats. Thirty minutes following onset of intranasal delivery, rats were perfused with saline and fixed with 4% paraformaldehyde. Gamma counting was used to evaluate $^{125}$I-HC concentration and distribution in the CNS, peripheral tissues and blood. The DTI for each tissue was calculated by dividing the ratio of mean tissue concentration to blood area under the curve (AUC) of the vasoconstrictor group by the ratio of mean tissue concentration to blood AUC of the control group. DTI >1.0 indicated a drug targeting advantage with the vasoconstrictor.

Results

HC plus 0.1% THZ (Refer to Table 3)

Addition of 0.1% THZ to the intranasal formulation of HC reduces elimination and clearance of HC from the olfactory epithelium into the bloodstream. 0.1% THZ significantly reduces the concentration in the blood at 5 min (1.1 nM vs. 0.4 nM, p=0.02) and significantly increases the concentration in the olfactory epithelium (1024 nM vs. 6744 nM, p=0.04) compared to controls. There is a significant increase in delivery to the olfactory bulbs (2.1 nM vs. 3.3 nM, p=0.03). In addition, there is a trend towards reducing delivery to the kidney (6.6 nM vs. 4.3 nM, p=0.08). The drug targeting index for the liver, kidney, spleen and thyroid are less than 1.0, indicating that there is reduced drug targeting to these peripheral organs in the presence of 0.1% THZ, thereby minimizing side effects and toxicity.

In addition, incorporation of 0.1% THZ in the intranasal formulation of HC resulted in fewer incidences of respiratory distress in animals during intranasal delivery.

HC plus 0.1% THZ Following Pre-Treatment of Nasal Cavity with 0.1% THZ (Refer to Table 4)

Pre-treatment with and addition of 0.1% THZ to the intranasal formulation of HC reduces absorption of HC into the blood and reduces delivery of HC to peripheral organs. Delivery of HC to caudal brain tissues and the spinal cord is also reduced with pre-treatment with 0.1% THZ, while delivery to rostral brain tissues remains unchanged.

Absorption of HC into the blood is significantly decreased, particularly at 10 minutes (1.1 nM vs. 0.6 nM, p=0.03), 15 minutes (2.0 nM vs. 1.2 nM, p=0.01), and 20 minutes (3.1 nM vs. 2.1 nM, p=0.03).

Pre-treatment with 0.1% THZ significantly reduces delivery to the kidney (3.9 nM vs. 1.7 nM, p=0.01) and thyroid (276 nM vs. 68 nM, p=0.002). In addition, the drug targeting index for the muscle, kidney, spleen and thyroid are less than 1.0, indicating that there is reduced targeting to these peripheral organs by pre-treating the nasal cavity with 0.1% THZ. Significantly lower concentrations of HC are found in the trachea (49 nM vs. 2.0 nM, p=0.003) and esophagus (130 nM vs. 0.7 nM, p=0.06) and it was observed that there was significantly fewer signs of respiratory distress in rats treated with 0.1% THZ.

Pre-treatment of the nasal cavity with 0.1% THZ, followed by intranasal delivery of HC plus 0.1% THZ results in significantly reduced delivery to caudal brain regions, including the trigeminal nerve (5.5 nM vs. 2.0 nM, p=0.01), midbrain (0.7 nM vs. 0.5 nM, p=0.07), pons (0.8 nM vs. 0.5 nM, p=0.06) and cerebellum (0.6 nM vs. 0.4 nM, p=0.07). Additionally, significantly less HC is delivered to the upper cervical spinal cord (0.9 nM vs. 0.4 nM, p=0.002) and thoracic spinal cord (0.3 nM vs. 0.2 nM, p=0.06). Thus, 0.1% THZ reduces delivery to caudal brain regions, while having no effect on rostral brain regions such as the olfactory bulbs, anterior olfactory nucleus and frontal cortex. Inclusion of vasoconstrictors in the intranasal formulation of drugs provides a means to target delivery of therapeutic agents to specific brain regions.

HC plus 1% PHE Following Pre-Treatment of Nasal Cavity with 1% PHE (Refer to Table 4)

Pre-treatment with and addition of 1% PHE to the intranasal formulation of HC reduces elimination and clearance from the olfactory epithelium into the bloodstream. Delivery of HC to caudal brain regions is also reduced with pre-treatment with 1% PHE, while delivery to rostral brain regions is unaffected.

Pre-treatment of the nasal cavity with 1% PHE significantly decreases absorption of therapeutic compound HC into the blood stream at all time points (5 min: 0.3 nM vs. 0.03 nM, p=0.004, 10 min: 1.1 nM vs. 0.2 nM, p<0.001, 15 min: 2.0 nM vs. 0.3 nM, p <0.001, 20 min: 3.2 nM vs. 0.9 nM, p<0.001, 30 min: 3.2 nM vs. 1.1 nM, p<0.001). The deposition of HC in the olfactory epithelium is significantly enhanced (3861 nM vs. 14847 nM, p<0.001) following pre-treatment with 1% PHE.

In addition, pre-treatment of the nasal cavity with 1% PHE, followed by intranasal delivery of HC plus 1% PHE significantly decreases delivery of HC to the trigeminal nerve (5.5 nM vs. 2.2 nM, p=0.005) and caudal brain tissues, including the hippocampus (0.6 nM vs. 0.4 nM, p=0.005), thalamus (0.6 nM vs. 0.4 nM, p=0.008), hypothalamus (1.4 nM vs. 0.7 nM, p=0.005), midbrain (0.7 nM vs. 0.5 nM, p=0.03), pons (0.8 nM vs. 0.5 nM, p=0.03), and cerebellum (0.6 nM vs. 0.4 nM, p=0.03).

Pre-treatment of the nasal cavity with 1% PHE results in an approximate 2.5 fold enhancement of therapeutic compound targeting to the central nervous system. 1% PHE enhances targeting to the brain and spinal cord, while significantly reducing absorption into the blood stream.

Pre-treatment with 1% PHE significantly reduces delivery of the therapeutic compound to peripheral organs including the spleen (0.9 nM vs. 0.6 nM, p=0.05) and thyroid (276 nM vs. 77 nM, p=0.003). In addition, the drug targeting index for the muscle is less than those for brain tissues, indicating that 1% PHE reduces targeting to the muscle, while enhancing targeting to the brain and spinal cord.

Pre-treatment with and use of 1% PHE significantly effects delivery of therapeutic compound HC to the lymphatic system. Pre-treatment with 1% PHE results in significant increases in delivery of HC to the superficial cervical lymph nodes (5.1 nM vs. 9.2 nM, p=0.05) and deep cervical lymph nodes (13 nM vs. 29 nM, p=0.04). 1% PHE also causes a significant decrease in delivery to the axillary lymph nodes (0.9 nM vs. 0.5 nM, p=0.006).

In addition, incorporation of 1% PHE in the intranasal formulation improved the consistency in delivery to the olfactory epithelium, but did not lead to any improvement in respiration during intranasal delivery.

Conclusion for Exemplary Experiment and Data Set 2

Use of 0.1% THZ in the formulation of HC and other therapeutic compounds decreases the amount of therapeutic compound entering the blood stream at early times, and thus reduces systemic exposure, exposure to peripheral tissues and unwanted systemic side effects. Use of 0.1% THZ increases targeting of the therapeutic compound to the olfactory epithelium and olfactory bulbs. In addition, there is reduced drug targeting to peripheral tissues (liver, kidney, spleen, thyroid).

Pre-treatment with and use of 0.1% THZ in the formulation of HC and other drugs significantly reduces absorption into the blood stream at most time points and decreases drug targeting to peripheral tissues. Pre-treatment with 0.1% THZ decreases delivery of HC to caudal portions of the brain, while leaving rostral portions unaffected. Incorporation of 0.1% THZ in the pharmaceutical composition also improves respiration in animals during intranasal delivery.

Pre-treatment with and use of 1% PHE in the formulation of HC and other therapeutic compounds significantly decreases the amount of drug entering the blood stream at all time points and thus reduces systemic exposure and unwanted systemic side effects. Pre-treatment with and use of 1% PHE in the formulation of HC and other therapeutic compounds enhances therapeutic compound targeting to the brain, spinal cord, olfactory epithelium and trigeminal nerve. Pre-treatment with and use of 1% PHE increases the consistency of delivery of therapeutic compounds to the brain, olfactory epithelium, olfactory bulbs, and trigeminal nerve.

Pre-treatment with and use of 1% PHE in the formulation of HC and other therapeutic compounds is more effective in reducing absorption into the blood stream and in enhancing therapeutic compound targeting to the brain and spinal cord compared to the use of 0.1% THZ.

Exemplary Experiment and Data Set 3

The effect of vasoconstrictors on intranasal drug targeting to the CNS of a smaller molecular weight therapeutic agent was also evaluated. We hypothesized that a therapeutic compound comprising a smaller peptide, which could more easily enter the blood, would be more affected by a vasoconstrictor than a therapeutic compound comprising a larger peptide. TP is a tripeptide with potent neuroprotective effects and is approximately one-tenth the size of HC.

Intranasal administration of $^{14}$C-TP in the presence of 1% PHE to anesthetized rats resulted in reduced absorption of therapeutic compound TP into the bloodstream at all time points over a 30 minute period (FIG. 4), which is consistent with our findings with HC discussed supra. In addition, 1% PHE reduced concentrations of TP in peripheral tissues including the lung, liver, heart, and kidney (FIG. 5).

In the presence of 1% PHE, intranasal targeting of TP, assessed by normalizing tissue concentrations to blood concentrations at 30 minutes, was increased to the olfactory epithelium, olfactory bulbs, rostral cortex and caudal cortex (Table 5). Drug targeting was also increased to the trigeminal nerve, meninges and lymphatics. With the exception of the increased drug targeting to the trigeminal nerve, these data with a considerably smaller peptide are consistent with the HC data. Therefore, the beneficial effect of a vasoconstrictor is not unique to HC and a vasoconstrictor can increase drug targeting with other therapeutic agents.

Exemplary Experiment and Data Set 4

We further evaluated the effect of vasoconstrictors on intranasal delivery of the therapeutic compound L-tyrosine-D-arginine, a stable dipeptide analog of the endogenous neuropeptide, kyotorphin (KTP, MW 337). KTP is a therapeutic compound demonstrating potent analgesic activity. The study investigated intranasal drug targeting of KTP to the CNS. First, to assess intranasal drug targeting of KTP to the CNS relative to intravenous administration, we compared the biodistribution of KTP following both routes of administration (n=6 to 7). Next, to assess if PHE enhances intranasal drug targeting of KTP to the CNS, we investigated the biodistribution of KTP following intranasal administration with 1% PHE (n=8). A higher concentration of PHE (5%) was also evaluated (n=6) to determine if the effect of the vasoconstrictor was dose dependent. Finally, CSF was sampled from a separate group of animals (n=4 to 6) after intravenous administration and intranasal administration of KTP in the presence and absence of 1% PHE.

Methods. A mixture of unlabeled and $^{125}$I-labeled neuropeptide (KTP) was administered to anesthetized rats. CNS tissues, peripheral tissues, and blood were sampled following perfusion and fixation of animals approximately 30 minutes after the onset of drug delivery. Concentrations were determined based on radioactivity measured in tissues and blood by gamma counting. CNS tissue concentrations were normalized to blood concentrations at 30 minutes, providing an assessment of intranasal drug targeting to the CNS relative to the blood. Comparisons of concentrations and tissue-to-blood concentration ratios were made between different groups.

Animals. Adult male Sprague-Dawley rats (200-300 g; Harlan, Indianapolis, Ind.) were housed under a 12-h light/dark cycle with food and water provided ad libitum. Animals were cared for in accordance with institutional guidelines and all experiments were approved by Regions Hospital, HealthPartners Research Foundation Animal Care and Use Committee.

Animal Surgeries. Animals were anesthetized with sodium pentobarbital (Nembutal, 50 mg/kg intraperitoneal, Abbott Laboratories, North Chicago, Ill.). Body temperature was maintained at 37° C. by insertion of a rectal probe connected to a temperature controller and heating pad (Fine Science Tools, Inc., Foster City, Calif.). For intranasal and intravenous experiments, the descending aorta was cannulated for blood sampling and perfusion using a 20 G, 1¼ inch catheter (Jelco, Johnson and Johnson Medical Inc., Arlington, Tex.) connected to a 3-way stopcock (B. Braun Medical Inc., Bethlehem, Pa.). In addition, for intravenous experiments, the femoral vein was cannulated for drug administration using a 25 G, ¾ inch catheter (Becton Dickinson, Franklin Lakes, N.J.) connected to tubing and a 3-way stopcock (B. Braun Medical Inc., Bethlehem, Pa.).

Preparation of Formulations. Intranasal and Intravenous Dose Solutions contained a mixture of unlabeled and $^{125}$I-labeled neuropeptide (10 nmol, 50-55 µCi) dissolved in PBS (10 mM sodium phosphate, 154 mM sodium chloride, pH 7.4) to a final volume of 48 µL and 500 µL, respectively. For intranasal experiments with vasoconstrictor, 10% PHE (w/v) or 50% PHE (w/v) stock solutions were prepared and added to dose solutions containing neuropeptide to make a final concentration of 1% PHE or 5% PHE, respectively. Dose solution aliquots for each experiment were stored at −20° C. until the day of the experiment.

Drug Administration. Intranasal administration was performed with animals lying on their backs and rolled gauze (1¼ cm diameter) placed under the neck to maintain rat head position, which prevented drainage of the dose solution into the trachea and esophagus. A pipette (P20) was used to intranasally administer 48 µL of dose solution over 14 minutes. Eight-6 µL nose drops were given to alternating nares every two minutes while occluding the opposite naris. This method of administration was non-invasive as the pipette tip was not inserted into the naris, but rather, the drop was placed at the opening allowing the animal to snort the drop into the nasal cavity. Intravenous administration through the femoral vein was performed with animals lying on their backs using an infusion pump (Harvard Apparatus, Inc., Holliston, Mass.) to administer 500 µL of a solution containing an equivalent dose over 14 minutes.

Tissue and Fluid Sampling. Blood samples (0.1 mL) were obtained via the descending aorta cannula at 5, 10, 15, 20, and 30 minutes after the onset of drug delivery. After every other blood draw, 0.9% sodium chloride (0.35 mL) was replaced to maintain blood volume during the experiment.

Peripheral and CNS tissues were obtained at 30 minutes after the onset of drug delivery, following euthanasia of animals under anesthesia by perfusion and fixation through the descending aorta cannula with 60 mL of 0.9% sodium chloride and 360 mL of 4% paraformaldehyde in 0.1 M Sorenson's phosphate buffer using an infusion pump (15 mL/min; Harvard Apparatus, Inc., Holliston, Mass.). A gross dissection of major peripheral organs (muscle, liver, kidney, spleen, and heart) was performed, as well as dissection of the superficial and deep cervical lymph nodes and the axillary lymph nodes. The brain was removed and olfactory bulbs were dissected. Serial (2 mm) coronal sections of the brain were made using a rat brain matrix (Braintree Scientific, Braintree, Mass.). Microdissection of specific brain regions was performed on coronal sections using the Rat Brain Atlas as a reference. A posterior portion of the trigeminal nerve was dissected from the base of the cranial cavity from the anterior lacerated foramen to the point at which the nerve enters the pons. This tissue sample contained the trigeminal ganglion and portions of the ophthalmic (V1) and maxillary (V2) branches of the trigeminal nerve. Meninges from the spinal cord was removed and sampled prior to dissecting the spinal cord into cervical, thoracic, and lumbar sections. The left and right common carotid arteries were dissected from surrounding tissues with the aid of a dissection microscope. Each tissue sample was placed into a pre-weighed 5 mL tube, and the wet tissue weight was determined using a microbalance (Sartorius MC210S, Goettingen, Germany).

CSF was sampled via cisternal puncture at 30 minutes after the onset of drug delivery in a separate group of animals. Animals were placed on their ventral side over a rolled towel to position the head at a 45 degree angle. A 20 G needle attached to 30 cm long polyethylene tubing (PE90) was inserted into the cisterna magna. CSF was collected (~50 µL) into the tubing until flow stopped or until blood was observed. The tubing was immediately clamped if blood was observed to avoid contamination due to blood-derived radioactivity. Only CSF samples containing clear fluid were included in the analysis. Animals were perfused and fixed, and brain tissues were sampled as described above.

Sample and Data Analysis. Radioactivity in each tissue sample was determined by gamma counting in a Packard Cobra II Auto Gamma counter (Packard Instrument Company, Meriden, Conn.). Concentrations were calculated, under the assumption of minimal degradation of the $^{125}$I-labeled neuropeptides, using the specific activity of the $^{125}$I-labeled neuropeptide determined from standards sampled from the dose solution, counts per minute measured in the tissue following subtraction of background radioactivity, and tissue weight in grams.

Dose-normalized concentrations in blood, CNS tissues, and peripheral tissues from intranasal and intravenous experiments at 30 minutes were expressed as mean ±SE. Outliers were identified using the Grubbs statistical test for outliers and visually using box plots. The area under the blood concentration-time curve (AUC) from 0 to 30 minutes was calculated using the trapezoidal method without extrapolation to infinity. Since the concentrations observed in CNS after intranasal delivery could be due to absorption from the nasal vasculature and diffusion or receptor-mediated transport across the BBB, CNS tissue concentrations were normalized to blood concentrations at 30 minutes to assess direct transport from the nasal cavity. If the tissue-to-blood concentration ratios following intranasal delivery with PHE were observed to be greater than those after intravenous or intranasal administration without vasoconstrictor, then this would suggest that the vasoconstrictor enhances delivery along pathways other than vasculature. Intranasal drug targeting to the CNS could be enhanced with the vasoconstrictor if CNS tissue concentrations increased, if blood concentrations decreased or if both effects were observed. Unpaired two-sample t-tests were performed on concentrations and tissue-to-blood concentration ratios at 30 minutes to compare each group to intranasal control animals. Statistical analyses were performed using GraphPad Prism software (version 3.03, GraphPad Software Inc., San Diego, Calif.) and differences were significant if $p<0.05$.

Kyotorphin Biodistribution Following Intranasal and Intravenous Delivery. (See Table 6)

As illustrated by the data shown in Table 6 and accompanying figures, intranasal drug targeting of KTP to the CNS was confirmed by comparing intranasal and intravenous drug delivery. Intranasal compared to intravenous administration of KTP resulted in significantly lower concentrations in the blood at all time points measured (FIG. 6). Intranasal administration of KTP over 14 minutes resulted in a gradual increase in blood concentration, with a peak concentration of 11.7 nM at 30 minutes, while intravenous infusion resulted in a peak concentration of 83 nM at 10 minutes which steadily declined to 55 nM at 30 minutes. The resulting KTP blood AUC was significantly less following intranasal administration (145.30 nmol*min/L vs. 1708.83 nmol*min/L).

Intranasal administration resulted in KTP brain and spinal cord concentrations that were significantly lower than those after intravenous delivery (~3-fold); however the intravenous route was accompanied by 5-fold greater blood concentration. KTP brain concentrations after intranasal administration ranged from 1.8 nM to 4.3 nM, with the highest concentration in the olfactory bulbs. Intravenous brain concentrations ranged from 5.0 nM in the pons to 7.5 nM in the caudate/putamen. In the spinal cord, intranasal KTP resulted in a decreasing concentration gradient from the rostral to caudal direction, while intravenous delivery resulted in the highest concentration in the lumbar segment of the spinal cord. Distribution into the CSF and dorsal meninges were significantly greater with intravenous compared to intranasal administration. In the nasal cavity, the respiratory and olfactory epithelia contained very high levels of KTP following intranasal compared to intravenous administration. Superficial cervical lymph node concentrations were significantly greater with intravenous delivery, while deep cervical lymph node concentrations of KTP were significantly greater with intranasal delivery. No statistically significant differences were noted in trigeminal nerve concentrations ($p=0.41$), although KTP levels were slightly elevated in the intranasal group. Additionally, no statistically significant differences were observed in carotid artery concentrations; however concentrations were higher with intranasal delivery ($p=0.13$).

In peripheral tissues, intranasal delivery of KTP resulted in significantly lower concentrations compared to intravenous administration. The kidneys contained the highest peripheral tissue concentration of KTP, regardless of route of administration.

Kyotorphin Biodistribution With and Without PHE. Inclusion of PHE in intranasal formulations reduced absorption of KTP into the blood compared to intranasal KTP controls (FIG. 6). 1% PHE significantly reduced the KTP blood concentration at 30 minutes to 5.1 nM (56% reduction) and the blood AUC to 71.48 nmol*min/L (51% reduction). With 5% PHE, KTP blood concentration at 30 minutes was further reduced to 4.0 nM (66% reduction) and the KTP blood AUC was further reduced to 45.65 nmol*min/L (69% reduction) compared to intranasal KTP controls (FIG. 6).

PHE dose dependently increased concentrations of KTP in the olfactory bulbs to levels higher than those achieved with intravenous delivery, while reducing concentrations in most remaining brain regions (Table 6). As illustrated further by the data in Table 6, 1% PHE did not significantly affect concentrations of KTP in the anterior olfactory nucleus, but the presence of the vasoconstrictor significantly reduced concentrations by half to all remaining brain regions, as well as to the spinal cord. Similar trends were observed with 5% PHE, except fewer CNS tissues were significantly different from intranasal KTP controls. 1% PHE reduced KTP concentrations in the CSF from 0.5 nM to 0.3 nM, but these differences were only marginally significant ($p=0.09$). The effect of 5% PHE on CSF distribution of KTP was not evaluated. CSF concentrations of KTP were relatively low in comparison to concentrations in the brain, regardless of the route of drug administration. No significant effects on KTP concentrations in the meninges were noted with PHE.

Referring again to Table 6, in the nasal cavity, PHE dose dependently increased deposition in the olfactory epithelium. KTP olfactory epithelium concentrations were found to be predictive of olfactory bulb concentrations, with a positive correlation coefficient of 0.99 (data not shown). 1% PHE significantly increased KTP concentrations in the respiratory epithelium, while 5% PHE had no significant effect. PHE significantly increased KTP concentrations in superficial cervical lymph nodes from 6.5 nM to 21 nM with 1% PHE and to 13 nM with 5% PHE. KTP concentrations in the deep cervical lymph nodes were slightly elevated with PHE; however differences were not significant. Cervical lymph node concentrations were among the highest observed outside of the CNS following intranasal administration. No statistically significant differences were noted in trigeminal nerve concentrations with PHE; however these values were slightly reduced in the presence of vasoconstrictor. Additionally, no significant differences were observed in carotid artery concentrations, though 1% PHE reduced concentrations, while 5% PHE had little effect.

PHE significantly reduced exposure of KTP to all peripheral tissues sampled (except the heart with 5% PHE). Similar reductions in peripheral tissue concentrations were observed with 1% PHE and 5% PHE, with the greatest reduction in the kidney and liver.

Kyotorphin Drug Targeting to the CNS, Lymphatics, and Meninges. Intranasal compared to intravenous administration of KTP resulted in significantly greater brain tissue-to-blood concentration ratios, and 5% PHE, but not 1% PHE, significantly enhanced intranasal drug targeting of KTP to the brain and to the trigeminal nerve (See FIG. 7). The intranasal route of administration targeted KTP to the CNS compared to intravenous delivery, with the greatest tissue-to-blood concentration ratios in the trigeminal nerve (TN) and the olfactory bulbs (OB), while intravenous administration resulted in relatively uniform ratios throughout the CNS. 1% PHE significantly increased olfactory bulb ratios (5.3-fold increase) compared to intranasal KTP controls. No other significant differences in drug targeting were observed with 1% PHE (FIG. 10). With 5% PHE, intranasal drug targeting of KTP was increased to many more CNS tissues (FIG. 10). Compared to controls, 5% PHE significantly increased ratios in the olfactory bulbs (16.1-fold), anterior olfactory nucleus (AON, 3.2-fold), frontal cortex (FC, 2.3-fold), hippocampus (HC, 1.5-fold), hypothalamus (3.8-fold), and cerebellum (CB, 2.1-fold). In the spinal cord, drug targeting to the cervical spinal cord was increased with 5% PHE, but only marginally (p=0.07). Intranasal drug targeting was also significantly increased to the trigeminal nerve with 5% PHE (2.2-fold) (FIG. 7). Inclusion of 1% PHE or 5% PHE in nasal formulations also significantly enhanced targeting to the superficial nodes (5.1-fold and 4.6-fold, respectively) and to the cervical lymph nodes (3.0-fold and 4.8-fold, respectively) compared to intranasal KTP controls (data not shown). 1% PHE or 5% PHE also significantly enhanced targeting of KTP to the meninges, with slightly greater targeting to the ventral portion (3.6-fold and 3.4-fold, respectively) compared to the dorsal portion (2.3-fold and 3.2-fold, respectively).

Conclusion for Exemplary Experiment and Data Set 4

Our results indicate that over a 30 minute period, inclusion of a vasoconstrictor in the nasal formulation, or applied as a pretreatment prior to administering the therapeutic compound, drastically reduced blood concentrations and enhanced intranasal delivery to the CNS along olfactory neural pathways, while reducing transport along trigeminal pathways. PHE dose dependently increased concentrations of HC and KTP in the olfactory epithelium and olfactory bulbs, consistent with entry along olfactory nerves through the cribriform plate, suggesting that deposition in the olfactory region is critical for efficient delivery of intranasally applied drugs to rostral brain regions. Intranasal drug targeting, assessed by tissue-to-blood concentration ratios, was enhanced with PHE in certain CNS tissues, mainly due to the reduction in blood concentrations observed in the presence of the vasoconstrictor. Targeting to the olfactory bulbs was significantly greater with the 1% PHE formulation for HC and KTP. Enhanced drug targeting with 1% PHE was noted for HC throughout the brain, while no other significant differences in targeting of KTP was observed. These findings indicate that, at least for two therapeutic compounds comprising neuropeptides with different molecular weights, inclusion of a vasoconstrictor in nasal formulations can enhance drug targeting to rostral brain areas. Inclusion of PHE in the nasal formulation also enhanced drug targeting of HC and KTP to the lymphatic system and to the meningeal membranes surrounding the brain.

The data indicate that inclusion of a short-acting vasoconstrictor in a nasal formulation enhanced intranasal drug delivery and targeting to the olfactory bulbs, while significantly reducing absorption into the blood over a 30 minute time period, irrespective of the size of the therapeutic peptide, i.e., therapeutic compound administered. These findings provide additional evidence for olfactory-mediated pathways into rostral portions of the brain following intranasal administration. In addition, this work implicates mechanisms involving the trigeminal nerve and/or vasculature in intranasal delivery of therapeutics to the CNS. This novel strategy for enhancing intranasal delivery to the CNS using vasoconstrictors may be most suitable for potent CNS therapeutics that have adverse effects in the blood or peripheral tissues, that are rapidly degraded by enzymes in the blood or the gastrointestinal tract, or that are extensively bound by tissue or plasma proteins. Vasoconstrictor nasal formulations containing therapeutic compounds can be used to target brain tumors or to treat pain disorders, avoiding undesirable side effects that often accompany traditional routes of drug administration. Inclusion of vasoconstrictors in nasal formulations can result in enhanced therapeutic compound targeting to multiple brain areas, the lymphatic system, and the meninges, which may hold relevance for the treatment of various neurological disorders, autoimmune disorders, or meningitis.

Overall Conclusions

Intranasal administration, either targeting the upper one-third or lower two-thirds of the nasal cavity and/or without regard to intranasal target location(s), of therapeutics results in greater therapeutic compound or agent targeting to the CNS compared to intravenous delivery, and incorporation of a vasoconstrictor in the nasal formulation significantly enhances therapeutic compound targeting to the CNS, meninges and lymphatics, while significantly reducing absorption into the blood. This may be due to reduced clearance into the blood from the nasal cavity or due to decongestion of the nasal passages, allowing for increased residence time and contact with the olfactory mucosa. The potential application of vasoconstrictors in intranasal formulations are immense for highly potent drugs that have adverse effects in the blood or in peripheral tissues, that are rapidly degraded in the blood or in drug metabolizing organs, or that are extensively bound to plasma proteins. Vasoconstrictors could be used in nasal formulations of chemotherapeutics targeting brain tumors or with pain medications that target the brain and spinal cord, but that with traditional routes of administration, also result in undesirable side effects in patients. These data also show that intranasal delivery of immunotherapeutics in combination with a vasoconstrictor may be a successful drug targeting strategy to the immune system, as certain diseases involve the breakdown of the immune system and new therapeutics are emerging that activate the adaptive immune response to reject CNS tumors. We hypothesized that inclusion of a vasoconstrictor in nasal formulations, i.e., pharmaceutical compositions, would reduce absorption into the blood, increase the residence time of the therapeutic compound, e.g., drug, in the nasal epithelium, and facilitate intranasal delivery into the brain along pathways involving the olfactory nerves, trigeminal nerves, CSF or nasal lymphatic channels.

Several CNS-related disorders, diseases and/or conditions may be prevented, or the effects minimized, using different embodiments of the present invention. For example, and without limitation, patients at risk for Alzheimer's disease may be aided by the technique.

Further, in another embodiment, those patients scheduled for coronary artery bypass graft (CABG) surgery may also benefit due to the relatively high percentage of post-surgical cerebral ischemia.

In another embodiment, patients at risk for Parkinson's disease may benefit from the inventive method.

In yet another embodiment, patients at risk for stroke may be aided by the inventive method. Such patients would include those having risk factors comprising hypertension, diabetes, obesity, smoking, antiphospholipid syndrome or with a history of stroke (thus prone to subsequent stroke).

The above embodiments essentially focus on prevention of the cognitive, behavioral and physical impairment due to cerebral ischemia as a result of certain disorders or medical procedures. A series of alternate embodiments focus on treating such disorders after they have been diagnosed.

For example, again without limitation, in one embodiment, the inventive method may be used in a treatment plan for patients with Alzheimer's disease.

In another embodiment, the inventive method may be used to treat patients diagnosed with Parkinson's disease.

In yet another embodiment, patients diagnosed with stroke, and thus at risk for a subsequent stroke, may benefit from the inventive method.

In yet another embodiment, the inventive method may be used to treat patients diagnosed with narcolepsy.

In yet another embodiment, the inventive method may be used to treat patients diagnosed with other disorders of the central nervous system including: neurodegenerative disorders such as ALS and Huntington's disease, traumatic brain injury, spinal cord injury, epilepsy, hemorrhage, transient ischemic attacks, pain, depression, anxiety, schizophrenia, post traumatic stress disorder, personality disorder, autism, eating disorders, and other psychiatric or neurologic disorders.

In another embodiment, a pharmaceutical composition may be comprised of a combination of at least one therapeutic compound and at least one vasoconstrictor.

In another embodiment, at least one vasoconstrictor may be applied intranasally or otherwise, i.e., intravenously, topically as a pretreatment or concurrently with administration of at least one therapeutic compound. Further, at least one therapeutic compound may be combined with at least one vasoconstrictor to form a pharmaceutical compound that may be administered following pretreatment with intranasally (or intravenously, topically, etc.,) administered vasoconstrictor and/or concurrently with such vasoconstrictor.

In general, any of the therapeutic agents or pharmaceutical compositions described or referenced herein may be administered to under embodiments of the inventive method prior to a surgical procedure such as CABG, during such a procedure or after such a procedure.

In still another embodiment, the therapeutic agent according to the inventive methods may comprise one or more of the following substances which stimulate and/or stabilize HIF-1α: deferoxamine, insulin, IGF-I, heregulin insulin, IGF-I, heregulin, TGFbeta, IL1beta, TNFalpha, TGFbeta, cobalt, pyruvate, oxalacetate and lactate. It is within the scope of invention to create a pharmaceutical composition combining one or more of the foregoing substances with at least one vasoconstrictor. In addition, in other embodiments, the invention may administer a pharmaceutical composition comprising at least one of the foregoing substances with at least one metal chelator and at least one vasoconstrictor. Further, a pharmaceutical composition may be comprised in another embodiment of at least one of the foregoing substances combined with at least one antioxidant and at least one vasoconstrictor.

In addition, in other embodiments, the invention may administer a pharmaceutical composition comprising therapeutic compounds HC, TP, and/or KTP and at least one vasoconstrictor. Exemplary vasoconstrictors in the various embodiments of the present invention may comprise, without limitation, PHE and/or THZ. Additional vasoconstrictors will be well known to the skilled artisan and may include, again without limitation, methoxamine, phenylephrine, ephedrine, norepinephrine, oxymetazoline, tetrahydrozoline, xylometazoline, clonidine, guanabenz, guanfacine, α-methyldopa and/or arginine vasopressin.

An effective amount, as herein defined, of the therapeutic compound and/or vasoconstrictor to be administered pursuant to embodiments of the invention is the most preferred method of expression of dosage. Such effective amount is dependent upon many factors, including but not limited to, the type of disease or condition giving rise to an anticipated cerebral ischemic episode, the patient's general health, size, age, and the nature of treatment, i.e., short-term of chronic treatment. For illustrative purposes only, exemplary treatment regimens relating generally to the therapeutic compounds disclosed herein, including dosage ranges, volumes and frequency are provided below:

Efficacious dosage range: 0.0001-1.0 mg/kg.

A more preferred dosage range may be 0.005-1.0 mg/kg.

The most preferred dosage range may be 0.05-1.0 mg/kg.

The dosage volume (applicable to nasal sprays or drops) range may be 0.015 mls-1.0 mls.

The preferred dosage volume (applicable to nasal sprays or drops) range may be 0.03-0.6 mls.

The efficacious vasoconstrictor dosage may be 0.0001-0.3 mg/kg.

Generally, the treatment may be given in a single dose or multiple administrations, i.e., once, twice, three or more times daily over a period of time. For chronic disorders such as those diagnosed with, or at risk for, Alzheimer's disease, stroke or Parkinson's disease, the treatment may consist of at least one dose per day over an extended period of time. Alternatively, for those patients anticipating CABG surgery, the treatment may be a one-time dose to precondition the CNS in anticipation of potential cerebral ischemia. Such preconditioning may require more than one dose and may be administered from 12 hours to 1 week prior to the CABG surgery.

The brain concentrations that are likely to be achieved with the dosage ranges provided above are, for a single dose: 0.1 nM-50 μM. Over the course of a multi-dose treatment plan, the maximum brain concentration may be as high as 500 μM.

Inclusion of vasoconstrictors in intranasal formulations containing CNS therapeutic compounds for prevention and/or treatment of CNS-related and/or immune-related disorders, conditions and/or diseases:

(1) Reduces absorption into the blood, which is desirable for drugs with adverse side effects in the blood or in peripheral tissues;

(2) Reduces systemic drug exposure, which is important for drugs that are rapidly eliminated in drug metabolizing organs or for drugs that are extensively bound to plasma proteins;

(3) Targets drugs to the olfactory epithelium, reducing the need for expensive drug delivery devices that claim to target drugs to olfactory epithelium for CNS delivery of drugs;

(4) Reduces clearance of the drug into the blood from the nasal cavity, which increases the residence time and contact with the nasal epithelium;
(5) Targets drugs to the olfactory epithelium, olfactory bulbs and/or anterior olfactory nucleus to have therapeutic potential for the treatment of anosmia, which is associated with the onset of Alzheimer's disease and other neurologic disorders;
(6) Targets high potency drugs to the frontal cortex to reach brain targets involved in frontotemporal dementia, personality disorders, cognition disorders, motor dysfunction, and Alzheimer's disease;
(7) Targets the hippocampus for the treatment of learning and memory disorders associated with Alzheimer's disease and other neurologic disorders;
(8) Targets potent drugs to the hypothalamus for the treatment of eating or sleep disorders and for regulation of hormone function;
(9) Targets drugs to the cerebellum and brainstem for treating ataxia and Parkinson's disease and other motor disorders;
(10) Increases delivery and targeting of drugs to the lymphatic system to treat or prevent brain tumors, multiple myeloma, Hodgkin's disease, lymphadenitis, lymphatic filariasis, lymphoma, non-Hodgkin's lymphoma, thymus cancer and other forms of cancer, AIDS, neuroAIDS, SCID, autoimmune diseases, Sjogren's syndrome, chronic sinusitis, allergies, lupus and/or multiple sclerosis;
(11) Targets potent antibiotics or antiviral medications to the meninges surrounding the brain which can be used to treat meningitis or encephalitis; and
(12) Decongestant effects of vasoconstrictors can improve intranasal drug treatments of CNS disorders, lymphatic disorders, disorders of the meninges and other disorders in patients with nasal congestion due to colds or allergies.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

TABLE 1

CONCENTRATIONS OF HC FOLLOWING INTRANASAL ADMINISTRATION IN THE PRESENCE AND ABSENCE OF 1% PHE

| Concentration (nM) | Intranasal HC Control Mean ± SE | Intranasal HC + 1% PHE Mean ± SE |
|---|---|---|
| Brain | | |
| Olfactory Bulbs | 2.68 ± 0.33 | 5.60 ± 0.49 * |
| Anterior Olfactory Nucleus | 1.11 ± 0.14 | 0.89 ± 0.07 |
| Frontal Cortex | 0.93 ± 0.09 | 0.69 ± 0.08 |
| Caudate/Putamen | 0.58 ± 0.08 | 0.40 ± 0.07 |
| Septal Nucleus | 0.88 ± 0.32 | 0.54 ± 0.12 |
| Parietal Cortex | 0.67 ± 0.07 | 0.39 ± 0.04 * |
| Hippocampus | 0.61 ± 0.06 | 0.32 ± 0.02 * |
| Thalamus | 0.60 ± 0.05 | 0.30 ± 0.02 * |
| Hypothalamus | 1.04 ± 0.11 | 0.68 ± 0.06 * |
| Midbrain | 0.65 ± 0.06 | 0.38 ± 0.03 * |
| Pons | 0.93 ± 0.14 | 0.44 ± 0.04 * |
| Medulla | 1.26 ± 0.22 | 0.76 ± 0.11 * |

TABLE 1-continued

CONCENTRATIONS OF HC FOLLOWING INTRANASAL ADMINISTRATION IN THE PRESENCE AND ABSENCE OF 1% PHE

| Concentration (nM) | Intranasal HC Control Mean ± SE | Intranasal HC + 1% PHE Mean ± SE |
|---|---|---|
| Cerebellum | 0.67 ± 0.07 | 0.38 ± 0.04 * |
| Spinal Cord | | |
| Cervical | 0.80 ± 0.12 | 0.96 ± 0.27 |
| Thoracic | 0.35 ± 0.03 | 0.19 ± 0.03 * |
| Lumbar | 0.35 ± 0.02 | 0.17 ± 0.01 * |
| Cerebrospinal Fluid | | |
| Cerebrospinal Fluid | 0.17 ± 0.02 | 0.28 ± 0.04 * |
| Meninges | | |
| Dorsal Meninges | 2.71 ± 0.33 | 1.51 ± 0.19 * |
| Ventral Meninges | 7.47 ± 1.19 | 7.54 ± 1.29 |
| Spinal Meninges | 2.66 ± 0.59 | 4.58 ± 1.47 |
| Nasal Epithelia | | |
| Respiratory Epithelium | 19921 ± 1758 | 11457 ± 1348 * |
| Olfactory Epithelium | 4241 ± 628 | 13330 ± 905 * |
| Lymphatic System | | |
| Superficial Cervical Nodes | 3.56 ± 0.25 | 6.50 ± 0.69 * |
| Deep Cervical Nodes | 18.29 ± 3.94 | 35.58 ± 3.54 * |
| Trigeminal Nerve | | |
| Trigeminal Nerve | 4.93 ± 0.70 | 1.71 ± 0.15 * |
| Blood Vessels | | |
| Carotid Arteries | 82.70 ± 13.13 | 256 ± 135 |
| Peripheral Tissues | | |
| Blood | 3.38 ± 0.16 | 1.19 ± 0.08 * |
| Muscle | 0.53 ± 0.05 | 0.40 ± 0.10 |
| Liver | 0.76 ± 0.05 | 0.69 ± 0.04 |
| Kidney | 3.00 ± 0.30 | 2.75 ± 0.47 |
| Spleen | 0.89 ± 0.06 | 0.50 ± 0.04 * |
| Heart | 0.37 ± 0.06 | 0.18 ± 0.02 * |

$p < 0.05$, unpaired t-test comparing intranasal HC + 1% PHE with intranasal HC control

TABLE 2

ENHANCED DRUG TARGETING WITH VASOCONSTRICTOR IN THE INTRANASAL FORMULATION

| DRUG TARGETING | IN vs. IV Fold Difference | IN PHE vs. IV Fold Difference | IN PHE vs. IN Fold Difference |
|---|---|---|---|
| Olfactory Epithelium | 3176 | 31852 | 10 |
| Trigeminal Nerve | 12 | 12 | 1.0 |
| Olfactory Bulbs | 11 | 72 | 6.8 |
| Anterior Olfactory Nucleus | 6.7 | 16 | 2.3 |
| Frontal Cortex | 5.1 | 12 | 2.3 |
| Hippocampus | 3.9 | 6.0 | 1.5 |
| Hypothalamus | 5.9 | 11 | 1.8 |
| Pons | 5.6 | 9.0 | 1.6 |
| Cerebellum | 5.0 | 7.0 | 1.4 |
| Upper Cervical Spinal Cord | 17.4 | 16 | 0.9 |
| Lower Cervical Spinal Cord | 4.5 | 14 | 3.0 |
| Thoracic Spinal Cord | 2.7 | 4.7 | 1.7 |
| Lumbar Spinal Cord | 1.8 | 2.5 | 1.4 |
| Dorsal Meninges | 8.3 | 12 | 1.5 |
| Ventral Meninges | 16 | 37 | 2.3 |
| Superficial Lymph Nodes | 5.6 | 32 | 5.7 |
| Deep Cervical Lymph Nodes | 32 | 164 | 5.1 |
| Axillary Lymph Nodes | 0.9 | 1.3 | 1.3 |

Drug targeting = (Brain/blood)$_{intranasal}$/(Brain/blood)$_{intravenous}$

TABLE 3

CONCENTRATIONS OF HC FOLLOWING INTRANASAL ADMINISTRATION IN THE ABSENCE
AND PRESENCE OF 0.1% THZ WITH NO PREATREATMENT OF THE NASAL CAVITY

|  | Control<br>n = 4, 43 µL, 40 µCi, 10 nmol | | 0.1% THZ-treated<br>n = 4, 44 µL 43 µCi, 11 nmol | | |
|---|---|---|---|---|---|
| CONCENTRATION (nM) | MEAN | SE | MEAN | SE | *p < 0.05 |
| Blood at 30 minutes | 5.61 | 0.86 | 5.82 | 0.52 | |
| Olfactory Epithelium | 1023.94 | 462.33 | 6744.60 | 2132.99 | * |
| Trigeminal Nerve | 5.38 | 1.12 | 3.43 | 0.63 | |
| Olfactory Bulbs | 2.11 | 0.24 | 4.82 | 1.55 | |
| Anterior Olfactory Nucleus | 1.13 | 0.08 | 1.50 | 0.42 | |
| Frontal Cortex | 1.31 | 0.12 | 1.46 | 0.39 | |
| Hippocampus | 0.71 | 0.03 | 0.87 | 0.31 | |
| Hypothalamus | 1.89 | 0.14 | 1.97 | 0.58 | |
| Pons | 0.90 | 0.05 | 0.83 | 0.25 | |
| Cerebellum | 0.75 | 0.05 | 0.79 | 0.24 | |
| Upper Cervical Spinal Cord | 1.40 | 0.15 | 1.22 | 0.62 | |
| Lower Cervical Spinal Cord | 0.78 | 0.36 | 0.60 | 0.15 | |
| Thoracic Spinal Cord | 0.48 | 0.15 | 0.33 | 0.02 | |
| Lumbar Spinal Cord | 0.49 | 0.12 | 0.37 | 0.03 | |
| Dorsal Meninges | 3.35 | 0.48 | 3.88 | 1.00 | |
| Ventral Meninges | 6.46 | 1.95 | 6.68 | 1.39 | |
| Superficial Lymph Nodes | 14.86 | 2.82 | 21.97 | 4.77 | |
| Deep Cervical Lymph Nodes | 24.70 | 6.83 | 24.38 | 6.36 | |
| Axillary Lymph Nodes | 1.36 | 0.13 | 1.30 | 0.36 | |
| Muscle | 0.65 | 0.16 | 0.74 | 0.22 | |
| Liver | 1.89 | 0.30 | 1.85 | 0.27 | |
| Kidney | 6.56 | 0.87 | 5.55 | 1.28 | |
| Spleen | 3.75 | 2.10 | 1.27 | 0.18 | |

*p < 0.05, unpaired t-test between control and 0.1% THZ-treated

TABLE 4

CONCENTRATIONS OF HC FOLLOWING INTRANASAL ADMINISTRATION IN THE ABSENCE
AND PRESENCE OF VASOCONSTRICTORS WITH PREATREATMENT OF THE NASAL CAVITY

|  | Control<br>n = 7, 48 µL 40 µCi, 10 nmol | | 0.1% THZ-treated<br>n = 8, 48 µL, 40 µCi, 10 nmol | | 1% PHE-treated<br>n = 8, 48 µL, 40 µCi, 10 nmol | |
|---|---|---|---|---|---|---|
| CONCENTRATION (nM) | MEAN | SE | MEAN | SE | MEAN | SE |
| Blood at 30 minutes | 3.16 | 0.32 | 3.23 | 0.81 | 1.09# | 0.07 |
| Olfactory Epithelium | 3860.77 | 1376.05 | 3834.99 | 1866.37 | 14846.60# | 958.80 |
| Trigeminal Nerve | 5.48 | 0.75 | 2.02* | 0.64 | 2.23# | 0.60 |
| Olfactory Bulbs | 3.52 | 0.90 | 3.55 | 1.54 | 6.54 | 1.36 |
| Anterior Olfactory Nucleus | 1.33 | 0.23 | 0.79 | 0.16 | 0.90 | 0.13 |
| Frontal Cortex | 1.26 | 0.15 | 0.84 | 0.21 | 0.94 | 0.15 |
| Hippocampus | 0.63 | 0.07 | 0.45 | 0.06 | 0.38# | 0.04 |
| Hypothalamus | 1.35 | 0.16 | 0.81 | 0.20 | 0.73# | 0.10 |
| Pons | 0.81 | 0.10 | 0.49 | 0.09 | 0.51# | 0.08 |
| Cerebellum | 0.63 | 0.06 | 0.44 | 0.06 | 0.43# | 0.06 |
| Upper Cervical Spinal Cord | 1.36 | 0.45 | 0.40 | 0.06 | 1.36 | 0.50 |
| Lower Cervical Spinal Cord | 0.54 | 0.23 | 0.24 | 0.03 | 0.89 | 0.42 |
| Thoracic Spinal Cord | 0.32 | 0.05 | 0.21 | 0.03 | 0.21 | 0.05 |
| Lumbar Spinal Cord | 0.33 | 0.02 | 0.27 | 0.04 | 0.18# | 0.02 |
| Dorsal Meninges | 2.89 | 0.55 | 1.97 | 0.75 | 1.71 | 0.43 |
| Ventral Meninges | 6.71 | 1.32 | 4.75 | 1.93 | 6.52 | 2.56 |
| Superficial Lymph Nodes | 5.06 | 1.16 | 9.03 | 2.53 | 9.15# | 1.43 |
| Deep Cervical Lymph Nodes | 12.89 | 2.07 | 12.68 | 5.50 | 29.01# | 6.31 |
| Axillary Lymph Nodes | 0.94 | 0.13 | 0.65 | 0.08 | 0.50# | 0.05 |
| Muscle | 1.21 | 0.78 | 0.33 | 0.07 | 0.46 | 0.17 |
| Liver | 0.88 | 0.11 | 0.72 | 0.11 | 0.82 | 0.06 |
| Kidney | 3.93 | 0.68 | 1.73* | 0.26 | 3.47 | 0.96 |
| Spleen | 0.88 | 0.13 | 0.65 | 0.07 | 0.57# | 0.07 |

*p < 0.05, unpaired t-test between control and 0.1% THZ-treated;
p < 0.05, unpaired t-test between control and 1% PHE-treated

TABLE 5

TISSUE-TO-BLOOD RATIOS OF TP FOLLOWING INTRANASAL ADMINISTRATION IN THE ABSENCE AND PRESENCE OF 1% PHE

| TISSUE-TO-BLOOD RATIO | Control (n = 2) MEAN | SE | PHE-treated (n = 2) MEAN | SE |
|---|---|---|---|---|
| Olfactory Epithelium | 1741.73 | 257.59 | 10622.99 | 6537.86 |
| Trigeminal Nerve | 2.82 | 0.24 | 11.30 | 2.88 |
| Olfactory Bulbs | 9.04 | 4.78 | 45.77 | 4.18 |
| Rostral Cortex | 0.90 | 0.26 | 2.05 | 0.18 |
| Caudal Cortex | 0.82 | 0.09 | 1.03 | 0.09 |
| Hippocampus | 0.93 | 0.17 | 0.93 | 0.19 |
| Midbrain | 0.94 | 0.17 | 1.23 | 0.06 |
| Pons | 0.96 | 0.14 | 1.31 | 0.29 |
| Cerebellum | 1.06 | 0.15 | 1.22 | 0.20 |
| Upper Cervical Spinal Cord | 1.38 | 0.71 | 1.08 | 0.19 |
| Lower Cervical Spinal Cord | 0.68 | 0.05 | 0.56 | 0.01 |
| Thoracic Spinal Cord | 0.55 | 0.07 | 0.52 | 0.09 |
| Lumbar Spinal Cord | 0.56 | 0.12 | 0.51 | 0.07 |
| Ventral Meninges | 7.84 | 1.85 | 63.96 | 19.36 |
| Superficial Lymph Nodes | 2.98 | 1.15 | 27.33 | 9.16 |
| Deep Cervical Lymph Nodes | 34.35 | 10.08 | 99.63 | 15.07 |

TABLE 6

CONCENTRATIONS OF KTP FOLLOWING INTRAVENOUS ADMINISTRATION AND INTRANASAL ADMINISTRATION OF KTP IN THE PRESENCE AND ABSENCE OF PHE

| Concentration (nM) | Intravenous KTP Mean ± SE | Intranasal KTP Control Mea ± SE | Intranasal KTP + 1% PHE Mean ± SE | Intranasal KTP + 5% PHE Mea ± SE |
|---|---|---|---|---|
| Brain | | | | |
| Olfactory Bulbs | 6.88 ± 0.69 + | 4.33 ± 0.59 | 12.85 ± 3.28 * | 24.48 ± 4.64 # |
| Anterior Olfactory Nucleus | 6.18 ± 0.75 + | 2.42 ± 0.26 | 2.04 ± 0.41 | 2.70 ± 0.42 |
| Frontal Cortex | 6.60 ± 1.93 + | 2.24 ± 0.23 | 1.34 ± 0.20 * | 1.81 ± 0.23 |
| Caudate/Putamen | 7.54 ± 0.53 + | 2.13 ± 0.22 | 0.88 ± 0.13 * | 1.08 ± 0.29 # |
| Septal Nucleus | 6.64 ± 0.23 + | 2.09 ± 0.16 | 1.24 ± 0.12 * | 1.27 ± 0.21 # |
| Parietal | 7.30± + | 2.53 ± 0.12 | 1.13± | 1.28 ± 0.22 # |
| Hippocampus | 6.20± + | 1.90 ± 0.20 | 0.89± | 0.98 ± 0.20 # |
| Thalamus | 6.22± + | 1.83 ± 0.19 | 0.86± | 1.49 ± 0.49 |
| Hypothalamus | 7.03± + | 2.63 ± 0.25 | 1.66± | 3.64 ± 1.31 |
| Midbrain | 5.64± + | 1.92± | 0.96± | 1.49± |
| Pons | 4.97± + | 1.90± | 0.86± | 1.97± |
| Medulla | 5.33± + | 1.87± | 0.89± | 1.87± |
| Cerebellum | 5.98± + | 2.10± | 0.87± | 1.37± # |
| Spinal Cord | | | | |
| Cervical | 4.99 ± 0.72 + | 1.62 ± 0.40 | 0.64 ± 0.17 * | 1.37 ± 0.40 |
| Thoracic | 4.34 ± 0.49 + | 1.27 ± 0.24 | 0.52 ± 0.10 * | 0.50 ± 0.07 # |
| Lumbar | 5.46 ± 0.71 + | 1.20 ± 0.13 | 0.46 ± 0.06 * | 0.45 ± 0.03 # |
| Cerebrospinal Fluid | | | | |
| Cerebrospinal Fluid | 2.23 ± 0.17 + | 0.49 ± 0.09 | 0.27 ± 0.06 | — |
| Meninges | | | | |
| Dorsal Meninges | 6.26 ± 1.11 + | 4.34 ± 0.71 | 3.96 ± 0.84 | 6.43 ± 1.65 |
| Ventral Meninges | 10.32 ± 1.23 + | 16.66 ± 3.20 | 20.45 ± 2.91 | 20.22 ± 4.50 |
| Spinal Meninges | 10.12± | 5.59± | 3.48± | 2.88± |
| Nasal Epithelia | | | | |
| Respiratory Epithelium | 19.94± + | 21419± | 36853± | 15908± |
| Olfactory Epithelium | 30.67± + | 1988± | 5754± | 12492± # |
| Lymphatic System | | | | |
| Superficial Cervical Nodes | 10.50 ± 1.23 + | 6.45 ± 0.62 | 20.89 ± 3.39 * | 13.24 ± 1.32 # |
| Deep Cervical Nodes | 10.24 ± 1.15 + | 61.58 ± 18.42 | 71.48 ± 12.27 | 93.59 ± 12.01 |
| Trigeminal Nerve | | | | |
| Trigeminal Nerve | 9.44 ± 0.49 | 12.54 ± 3.33 | 7.68 ± 1.47 | 8.63 ± 1.61 |
| Blood Vessels | | | | |
| Carotid Artery | 18.74 ± 3.37 | 155.55 ± 77.26 | 69.20 ± 43.96 | 165.44 ± 56.5 |

TABLE 6-continued

CONCENTRATIONS OF KTP FOLLOWING INTRAVENOUS ADMINISTRATION AND INTRANASAL ADMINISTRATION OF KTP IN THE PRESENCE AND ABSENCE OF PHE

| Concentration (nM) | Intravenous KTP Mean ± SE | Intranasal KTP Control Mea ± SE | Intranasal KTP + 1% PHE Mean ± SE | Intranasal KTP + 5% PHE Mea ± SE |
|---|---|---|---|---|
| Peripheral Tissues | | | | |
| Blood | 54.88 ± 2.15 + | 11.68 ± 1.33 | 5.12 ± 0.47 * | 3.98 ± 0.30 # |
| Muscle | 13.62 ± 6.77 + | 2.20 ± 0.22 | 1.42 ± 0.23 * | 0.68 ± 0.04 # |
| Liver | 25.34 ± 4.66 + | 6.38 ± 1.12 | 1.70 ± 0.23 * | 1.58 ± 0.20 # |
| Kidney | 143.76 ± 50.94 + | 49.54 ± 9.46 | 7.19 ± 1.90 * | 7.39 ± 0.98 # |
| Splee | 12.51± + | 3.58± | 1.26± | 1.49± # |
| Heart | 3.72 ± 0.47 + | 1.46 ± 0.20 | 0.81 ± 0.08 * | 1.15 ± 0.25 |

+, *, # $p < 0.05$, unpaired t-test comparing each group with intranasal KTP control

What is claimed is:

1. A method for treating a disease or condition within a patient's brain, with increased targeting efficiency for at least one delivery target related to anatomical structures located in the rostral portion of the patient's brain compared to any delivery targets in the caudal portion of the patient's brain, and increased delivery of at least one therapeutic compound thereto compared with the caudal portion of the patient's brain, comprising:
   providing at least an effective amount of at least one therapeutic compound capable of treating the disease or condition;
   providing at least an effective amount of at least one vasoconstrictor;
   administering the at least an effective amount of the at least one therapeutic compound to the upper third of the patient's nasal cavity;
   administering the at least an effective amount of the at least one vasoconstrictor to the upper third of the patient's nasal cavity;
   thereby increasing targeting efficiency of the administered amounts of the at least one therapeutic compound to the patient's olfactory epithelium and thereby enabling at least an effective amount of the at least one therapeutic compound to bypass the patient's blood-brain barrier;
   delivering an effective amount of the at least one therapeutic compound to at least one target in the rostral portion of the patient's brain, with increased efficiency as compared with the delivery efficiency of the at least one therapeutic compound within the caudal portion of the patient's brain;
   minimizing the amount of the at least one therapeutic compound absorbed into the patient's blood and/or peripheral tissues; and
   treating the patient's disease or condition.

2. The method of claim 1, wherein the patient condition comprises Alzheimer's disease.

3. The method of claim 1, wherein the patient condition comprises Parkinson's disease.

4. The method of claim 1, wherein the patient condition comprises one or more of the following: cerebrovascular disorders, frontotemporal dementia, personality disorders, cognition disorders, motor dysfunction, eating disorders, sleep disorders, affective disorders, anxiety disorders, schizophrenia, brain tumors and ataxia.

5. The method of claim 1, wherein the at least one therapeutic compound comprises deferoxamine.

6. The method of claim 1, wherein the at least one therapeutic compound comprises one or more of the following: insulin, IGF-I, TGFbeta, IL1beta, TNFalpha, TGFbeta, cobalt, pyruvate, oxalacetate and lactate.

7. The method of claim 1, wherein the at least one therapeutic compound comprises one or more of the following: hypocretin-1 and kyotorphin.

8. The method of claim 1, wherein the at least one vasoconstrictor comprises phenylephrine and tetrahydrozoline.

9. The method of claim 1, wherein the condition comprises brain tumors and the method comprises treating brain tumors.

10. The method of claim 1, wherein the condition comprises one or more of the following: multiple myeloma, Hodgkin's disease, lymphadenitis, lymphatic filariasis, lymphoma, non-Hodgkin's lymphoma, and thymus cancer.

11. The method of claim 1, wherein the condition comprises one or more of the following: AIDS, neuroAIDS, SCID, autoimmune diseases, Sjogren's syndrome, lupus and multiple sclerosis.

12. The method of claim 1, wherein the condition comprises meningitis and/or encephalitis.

13. The method of claim 1, wherein the disease or condition comprises neurodegeneration.

14. A method for treating a disease or condition located within a patient's lymphatic system or meninges, with increased targeting efficiency for targets within the patient's lymphatics or meninges comprising:
   providing at least an effective amount of at least one therapeutic compound capable of treating the disease or condition;
   providing at least an effective amount of at least one vasoconstrictor;
   administering the at least an effective amount of the at least one therapeutic compound to the upper third of the patient's nasal cavity;
   administering the at least an effective amount of the at least one vasoconstrictor to the upper third of the patient's nasal cavity;
   thereby increasing targeting and delivery efficiency of the administered amounts of the at least one therapeutic compound to the patient's olfactory epithelium and thereby enabling at least an effective amount of the at least one therapeutic compound to bypass the patient's blood-brain barrier;
   delivering, with increased targeting and delivery efficiency, an effective amount of the at least one therapeutic compound to the patient's lymphatics or meninges as compared with an administration of the at least one therapeutic agent to the upper third of the patient's nasal cavity without administration of a vasoconstrictor;

minimizing the amount of the at least one therapeutic compound absorbed into the patient's blood and/or peripheral tissues; and treating the patient's disease or condition.

15. The method of claim 14, wherein the disease or condition within the patient's lymphatic system comprises one or more of the following: brain tumors, multiple myeloma, Hodgkin's disease, lymphadenitis, lymphatic filariasis, lymphoma, non-Hodgkin's lymphoma, thymus cancer and other forms of cancer, AIDS, neuroAlDS, SCID, autoimmune diseases, Sjogren's syndrome, chronic sinusitis, allergies, lupus, and multiple sclerosis.

16. The method of claim 14, wherein the disease or condition within the patient's meninges comprises one or more of meningitis and encephalitis.

\* \* \* \* \*